(12) United States Patent
Lee et al.

(10) Patent No.: US 11,793,070 B2
(45) Date of Patent: Oct. 17, 2023

(54) COMPOUND FOR ORGANIC ELECTRONIC ELEMENT, ORGANIC ELECTRONIC ELEMENT USING THE SAME, AND ELECTRONIC DEVICE THEREOF

(71) Applicant: DUK SAN NEOLUX CO., LTD., Cheonan-si (KR)

(72) Inventors: Yun Suk Lee, Seongnam-si (KR); Sun Hee Lee, Hwaseong-si (KR); Ki Ho So, Cheonan-si (KR); Dae Hwan Oh, Cheonan-si (KR); Hyoung Keun Park, Chuncheon-si (KR); Hye Min Cho, Goyang-si (KR); Jong Gwang Park, Ulsan (KR); Ga Eun Lee, Chungcheongbuk-do (KR); Yeon Seok Jeong, Gangwon-do (KR); Dae Sung Kim, Yongin-si (KR); Seong Je Park, Busan (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 267 days.

(21) Appl. No.: 15/743,924

(22) PCT Filed: Jul. 7, 2016

(86) PCT No.: PCT/KR2016/007400
§ 371 (c)(1),
(2) Date: Jan. 11, 2018

(87) PCT Pub. No.: WO2017/014460
PCT Pub. Date: Jan. 26, 2017

(65) Prior Publication Data
US 2018/0198072 A1   Jul. 12, 2018

(30) Foreign Application Priority Data

Jul. 17, 2015 (KR) .......................... 10-2015-0101433

(51) Int. Cl.
*H10K 85/60* (2023.01)
*C09K 11/06* (2006.01)
(Continued)

(52) U.S. Cl.
CPC ......... *H10K 85/654* (2023.02); *C07D 487/06* (2013.01); *C09K 11/06* (2013.01);
(Continued)

(58) Field of Classification Search
CPC ..... C07D 487/06; C07F 7/0812; C09K 11/06; H01L 51/0072; H10K 85/6572; H10K 85/631
See application file for complete search history.

(56) References Cited

U.S. PATENT DOCUMENTS

2005/0236970 A1\* 10/2005 Matsudate .......... H01L 27/3244
                                                              313/500
2012/0292576 A1\* 11/2012 Parham .................. C09B 21/00
                                                              252/500
(Continued)

FOREIGN PATENT DOCUMENTS

CN           104974166 A      10/2015
JP           2013-33804 A      2/2013
(Continued)

OTHER PUBLICATIONS

Chinese Office Action dated Nov. 13, 2019, for corresponding Chinese Patent Application No. 201680042161.4, 8 pages.

*Primary Examiner* — Sean M DeGuire
(74) *Attorney, Agent, or Firm* — Vorys, Sater, Seymour and Pease LLP; Mih Suhn Koh

(57) ABSTRACT

Provided is a novel compound capable of improving the luminous efficiency, stability and life span of a device, an organic electric element using the same, and an electronic device thereof.

14 Claims, 1 Drawing Sheet

(51) Int. Cl.
*C07D 487/06* (2006.01)
*H10K 50/16* (2023.01)
*H10K 50/18* (2023.01)
*H10K 50/81* (2023.01)
*H10K 50/82* (2023.01)
*H10K 50/17* (2023.01)
*H10K 71/00* (2023.01)
*H10K 50/15* (2023.01)
*H10K 85/30* (2023.01)

(52) U.S. Cl.
CPC .......... *H10K 50/16* (2023.02); *H10K 50/171* (2023.02); *H10K 50/18* (2023.02); *H10K 50/81* (2023.02); *H10K 50/82* (2023.02); *H10K 71/00* (2023.02); *H10K 85/631* (2023.02); *H10K 85/6572* (2023.02); *H10K 50/15* (2023.02); *H10K 50/156* (2023.02); *H10K 85/324* (2023.02)

(56) References Cited

U.S. PATENT DOCUMENTS

| | | | |
|---|---|---|---|
| 2015/0155524 A1* | 6/2015 | Liu | H01L 51/5262 257/40 |
| 2015/0179950 A1* | 6/2015 | Miyata | C07F 7/0812 548/406 |
| 2015/0179952 A1* | 6/2015 | Miyata | C07D 487/06 548/406 |

FOREIGN PATENT DOCUMENTS

| | | | | |
|---|---|---|---|---|
| KR | 10-2012-0129922 A | | 11/2012 | |
| KR | 10-2015-0002219 A | | 1/2015 | |
| KR | 2015002219 A | * | 1/2015 | .......... C07D 403/14 |
| KR | 10-2015-0073071 A | | 6/2015 | |
| KR | 10-2015-0073073 A | | 6/2015 | |
| KR | 10-2015-0114905 A | | 10/2015 | |
| KR | 10-2015-0131564 A | | 11/2015 | |

* cited by examiner

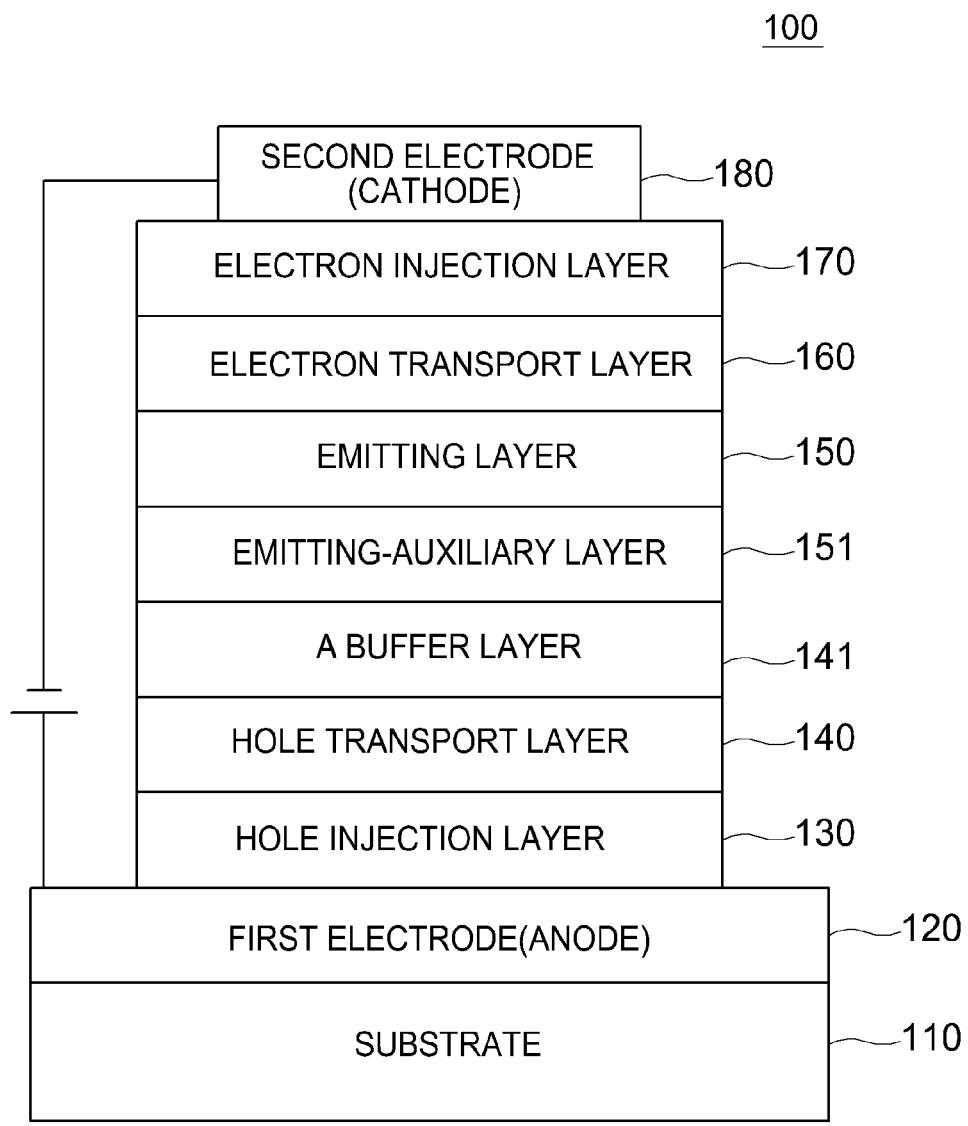

COMPOUND FOR ORGANIC ELECTRONIC ELEMENT, ORGANIC ELECTRONIC ELEMENT USING THE SAME, AND ELECTRONIC DEVICE THEREOF

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

The most problematic issues in an organic electric element are life span and efficiency, and as the display becomes larger, such efficiency and life span problems must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer can not maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, in order to solve the emission problem in the a hole transport layer in recent organic electric element, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has a low T1 value. As a result, the exciton generated in the emitting layer is transferred to the hole transport layer, resulting in charge unbalance in the emitting layer, and light is emitted at the interface of the hole transport layer.

When light is emitted from the interface of the hole transport layer, the color purity and efficiency of the organic electronic device are lowered and the life span is shortened. Therefore, it is urgently required to develop an emitting auxiliary layer having a high T1 value and a HOMO level between the HOMO energy level of the hole transport layer and the HOMO energy level of the emitting layer.

In addition, it is necessary to develop a hole injection layer material that retards penetration/diffusion of metal oxides from an anode electrode (ITO) into an organic material layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus it is necessary to develop a material that is durable to such a deposition method, that is, a highly heat-resistant material.

That is, in order to sufficiently exhibit the excellent characteristics of the organic electric element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electric element has not been sufficiently developed yet. Therefore, development of new materials is continuously required, and especially development of materials for the emitting-auxiliary layer and the hole transport layer is urgently required.

One prior art reference is as follows.
(Patent Document 1) KR 10-2013-00076842 A
(Patent Document 2) KR 10-2014-0103697 A

DETAILED DESCRIPTION OF THE INVENTION

Summary

In order to solve the problems of the background art described above, an embodiment of the present invention has revealed a compound having a novel structure, and also, it has been found that when this compound is applied to an organic electric device, the luminous efficiency, stability and lifetime of the device can be greatly improved.

An object of the present invention is to provide a compound, an organic electric element using the same and an electronic device thereof.

Technical Solution

The present invention provides a compound represented by Formula (1) below and a composition for a hole transport layer and an emitting-auxiliary layer comprising the same and an organic electric element characterized in having the same.

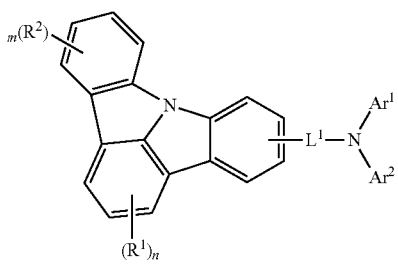

Formula (1)

Effects of the Invention

By using the compound according to the present invention, it is possible to achieve a high luminous efficiency, a low driving voltage, and a high heat resistance of the element, and can greatly improve the color purity and lifetime of the element.

BRIEF DESCRIPTION OF THE DRAWINGS

The FIGURE illustrates an example of an organic electric element according to the present invention.
- 100: organic electric element,
- 110: substrate
- 120: the first electrode(anode),
- 130: the hole injection layer
- 140: the hole transport layer,
- 141: a buffer layer
- 150: the emitting layer,
- 151: the emitting auxiliary layer
- 160: the electron transport layer,
- 170: the electron injection layer
- 180: the second electrode(cathode)

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected ", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxy group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and Polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and Polycyclic rings, and may include heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

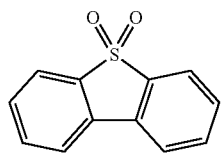 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds contain, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

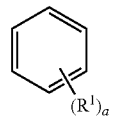

wherein, when a is an integer of zero, the substituent $R^1$ is absent, when a is an integer of 1, the sole substituent $R^1$ is linked to any one of the carbon constituting the benzene ring, when a is an integer of 2 or 3, they are respectively bonded as follows, in which $R^1$ may be the same as or different from each other, when a is an integer of 4 to 6, it bonds to the carbon of the benzene ring in a similar manner, and the indication of the hydrogen bonded to the carbon forming the benzene ring is omitted.

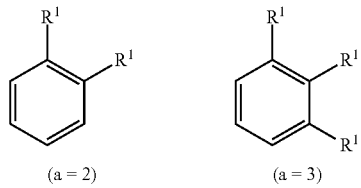

Hereinafter, a compound according to an aspect of the present invention and an organic electric element comprising the same will be described.

According to a specific example, the present invention provides a compound represented Formula (1) below.

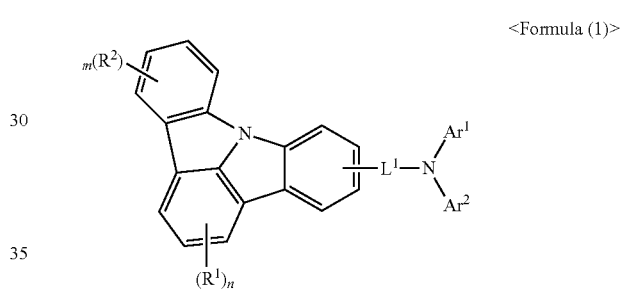

<Formula (1)>

In the Formula (1),

1) $Ar^1$ and $Ar^2$ are each independently selected from the group consisting of the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P), and $Ar^1$ and $Ar^2$ may combine with each other to form a ring, and may form a ring by bonding with adjacent $L^1$, 2) $L^1$ is a $C_6$-$C_{60}$ aryl group represented by the following Formula (1-a), and in the Formula (1-a), c represents an integer of 1 to 10 and is not substituted at the 1, 4 position of the aryl group,

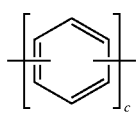
Formula (1-a)

3) m is an integer of 0 to 4, n is an integer of 0 to 3, and $R^1$ and $R^2$ are the same or different from each other and are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), and in case m and n are 2 or more, and are each in plural and are the same or different, and a plurality of $R^1$ or a plurality of $R^2$ may be bonded to each other to form a ring.

(where, aryl group, hetero aryl group, fluorenyl group, arylene group, heterocyclic group, fused ring group may be substituted by one or more of substituents selected from the group consisting of deuterium; halogen; a silane group; a siloxan group; a boron group; a germanium group; a cyano group; a nitro group; -L'-N($R_a$)($R_b$); a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted by deuterium; fluorenyl group; a $C_2$-$C_{20}$ heterocyclic group; a $C_3$-$C_{20}$ cycloalkyl group; a $C_7$-$C_{20}$ arylalkyl group, and a $C_8$-$C_{20}$ arylalkenyl group, and also may combine to each other to form a ring, wherein 'ring' means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.)}

According to a specific example, the Formula (1) provides the compound represented Formula (2) or Formula (3) below.

<Formula (2)>

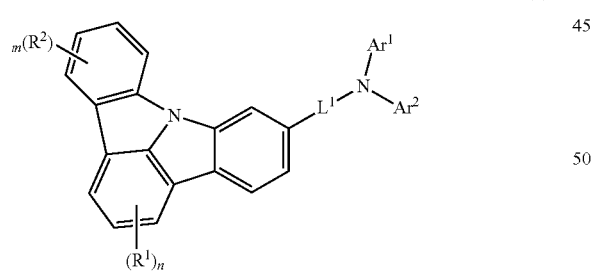

<Formula (3)>

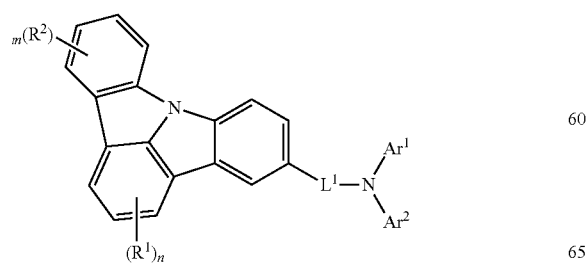

(in the Formula (2) or Formula (3), wherein $R^1$, $R^2$, $Ar^1$, $Ar^2$, m, n and $L^1$ are the same as defined in the Formula (1).)

More specially, the present invention provides a compound represented by Formula (2) or Formula (3) wherein $L^1$ is selected from the group consisting of the following Formulas (A-1) to (A-7).

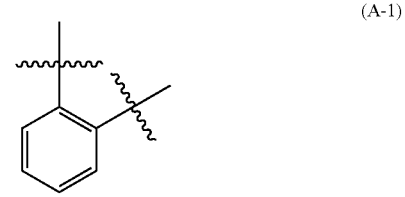
(A-1)

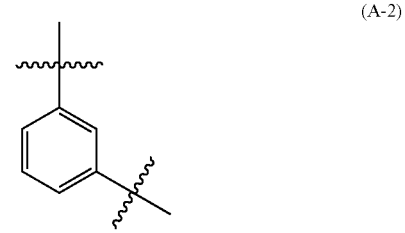
(A-2)

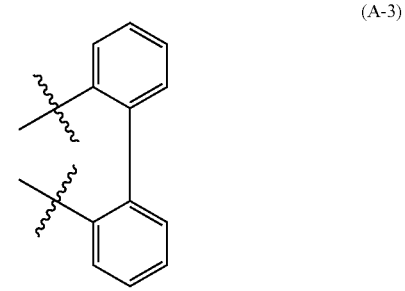
(A-3)

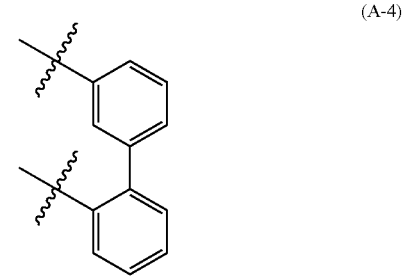
(A-4)

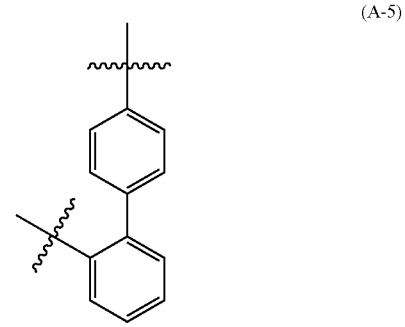
(A-5)

-continued
(A-6)
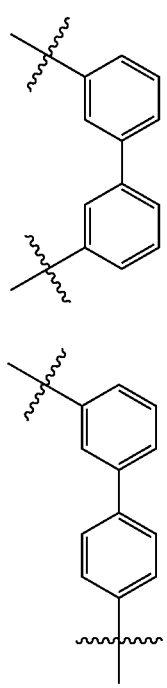
(A-7)
A more specific example of the present invention provides a compound represented by the Formulas.
1-1
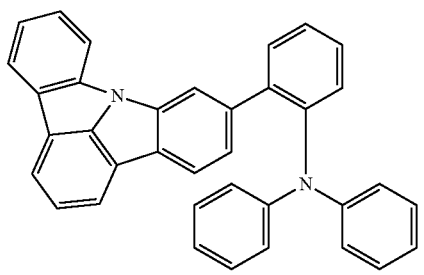
1-2
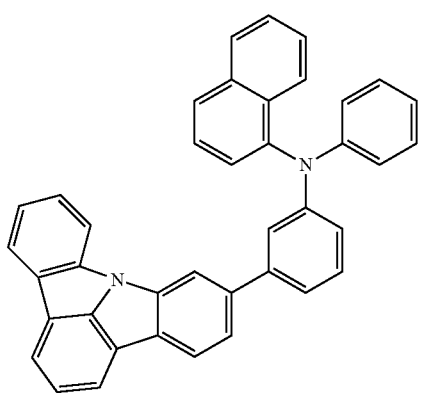
-continued
1-3
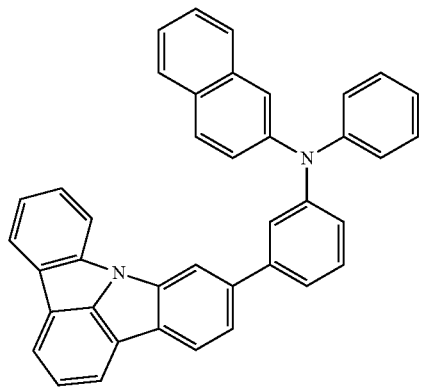
1-4
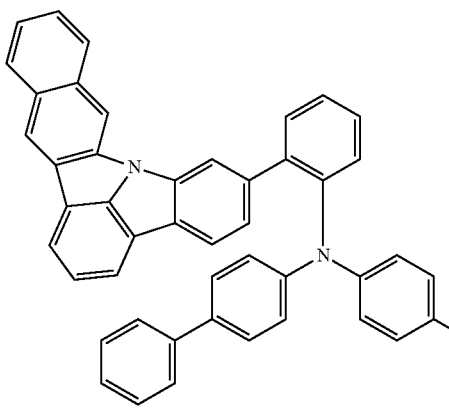
1-5
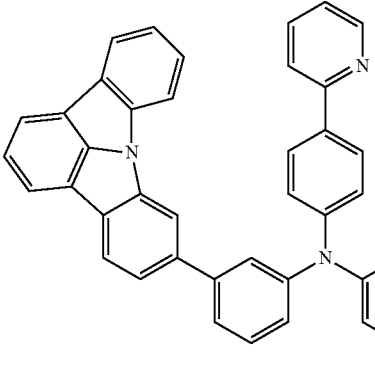
1-6
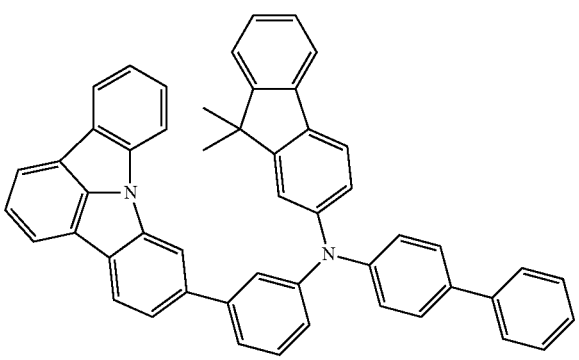

1-7
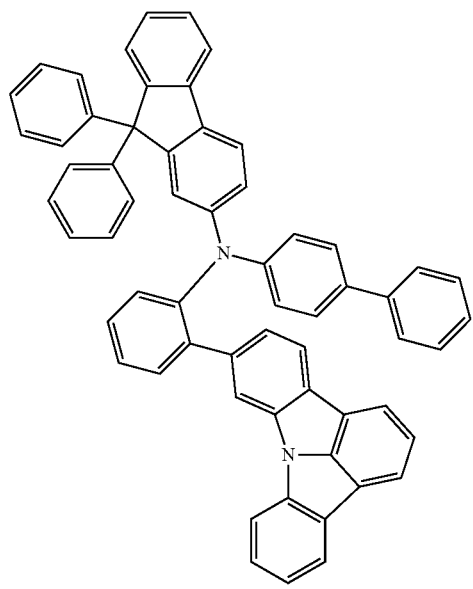
1-8
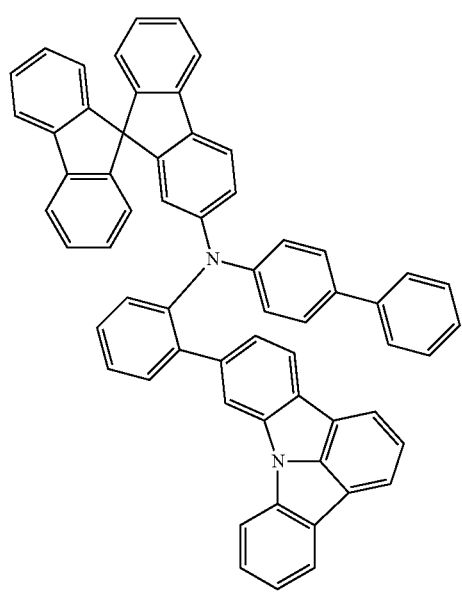
1-9
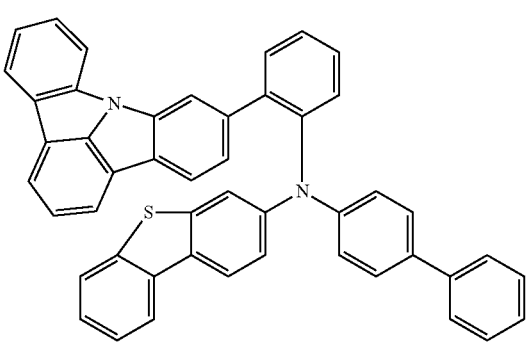
1-10
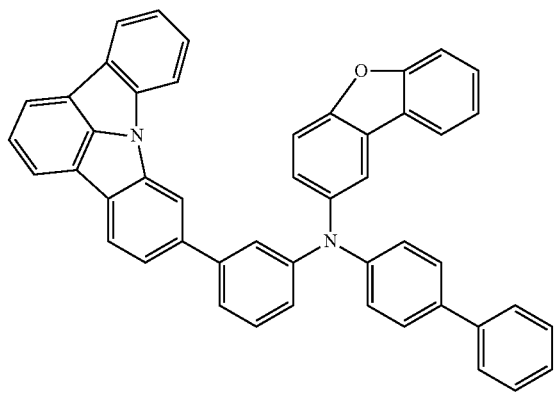
1-11
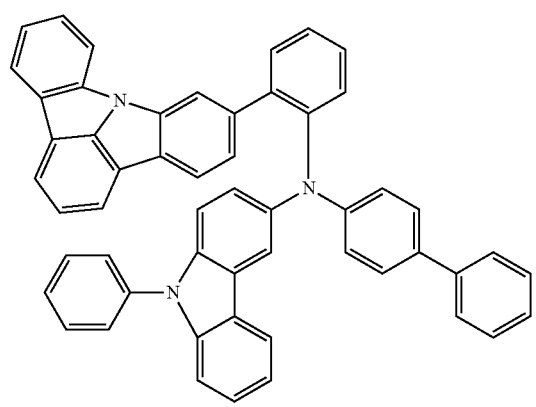
1-12
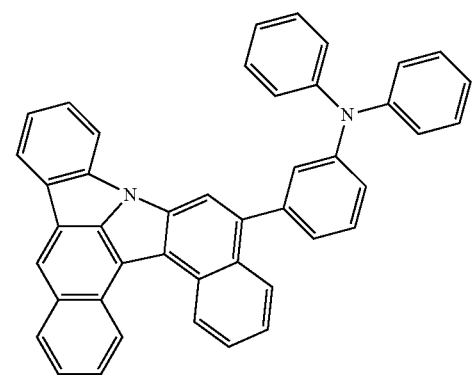
1-13
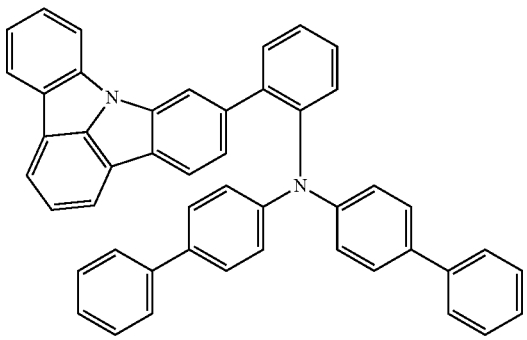

-continued
1-14
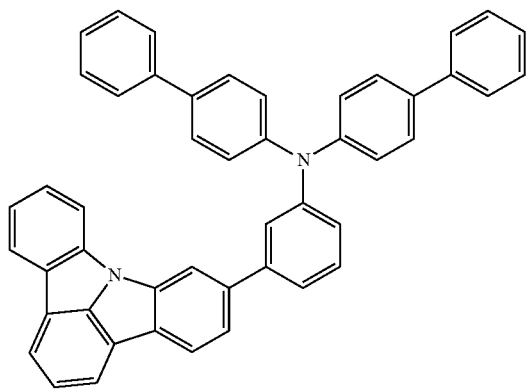
1-15
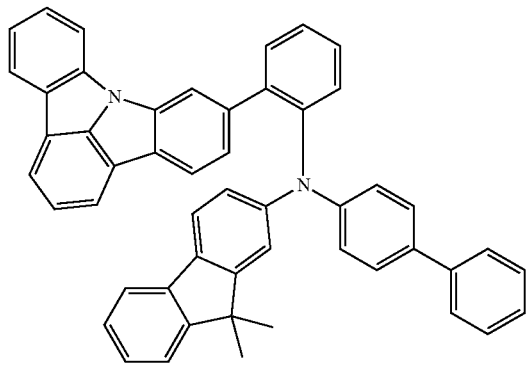
1-16
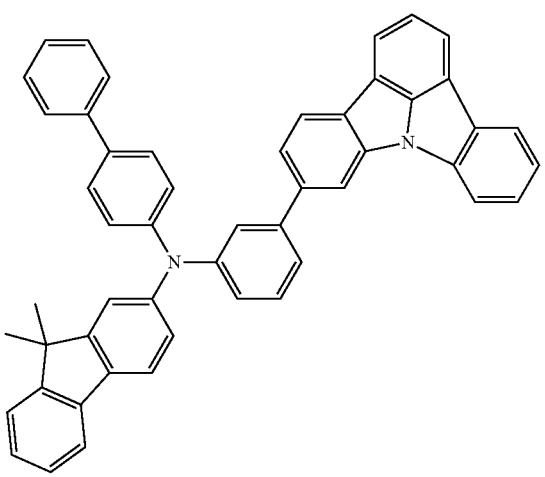
1-17
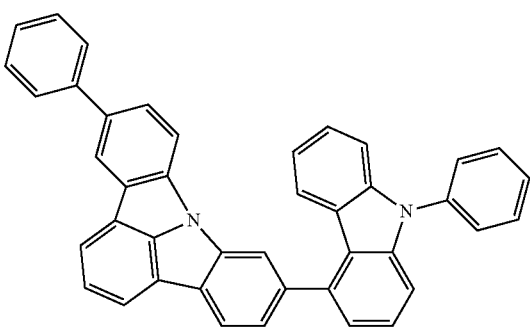
-continued
1-18
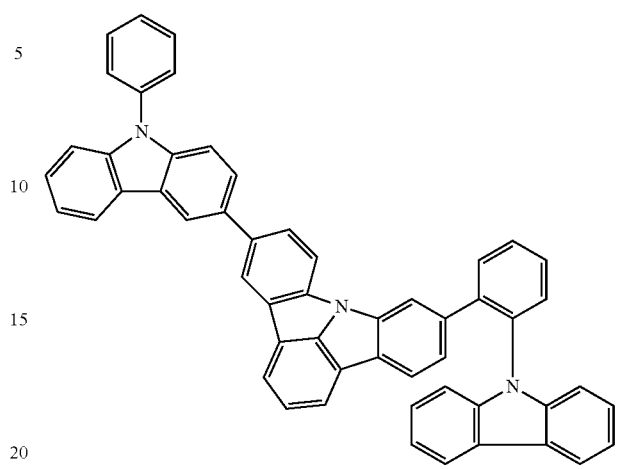
1-19
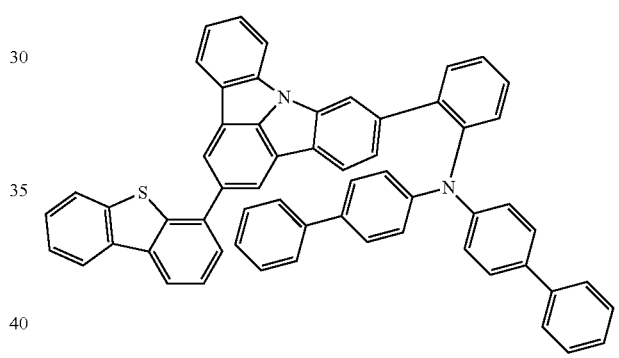
1-20
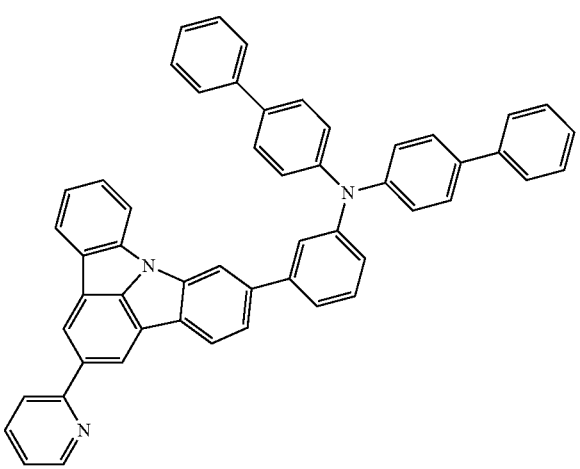

1-21
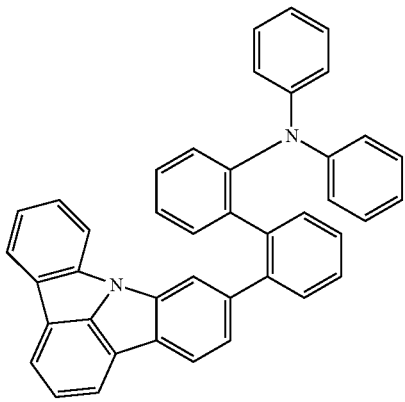
1-22
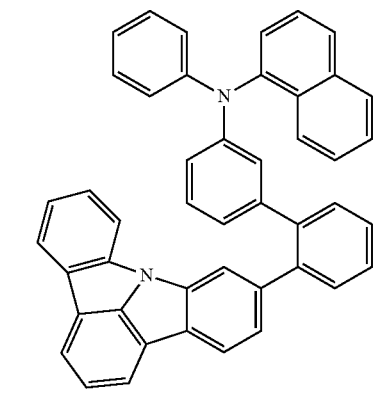
1-23
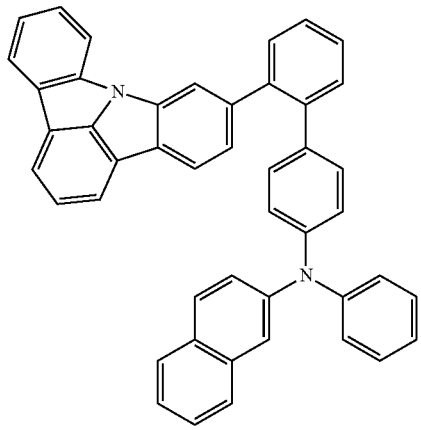
1-24
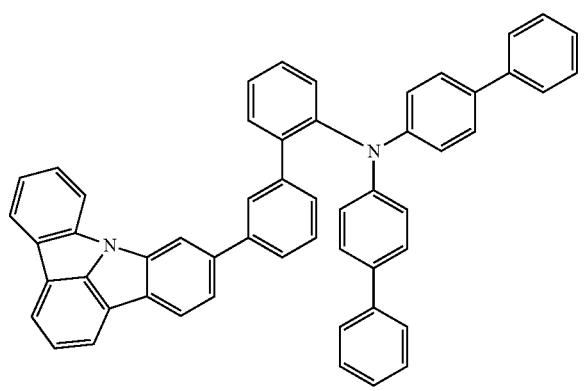
1-25
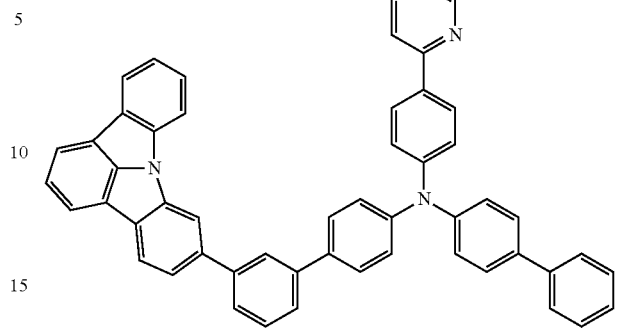
1-26
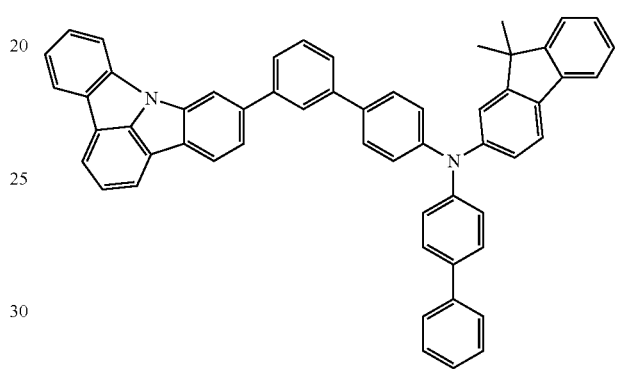
1-27
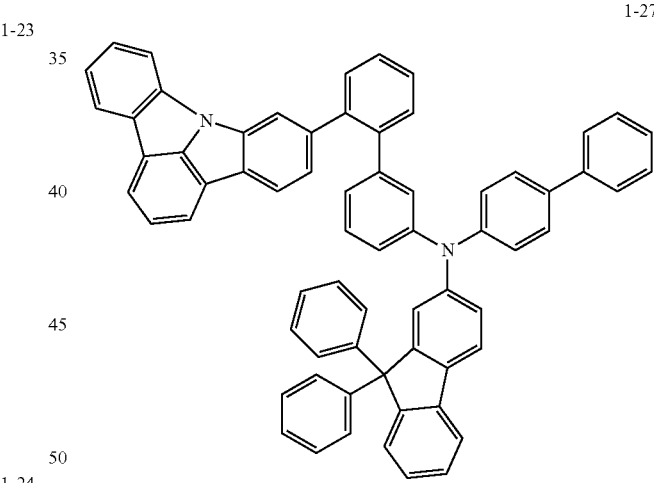
1-28
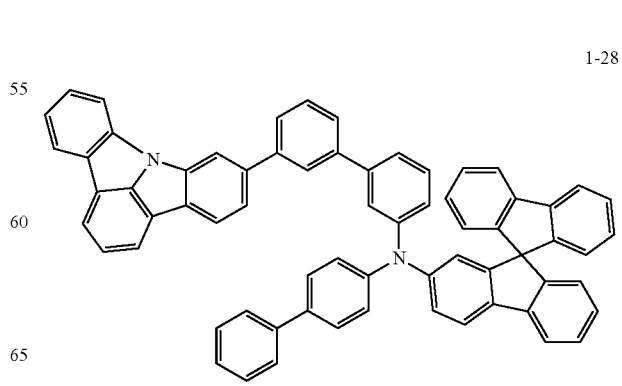

1-29
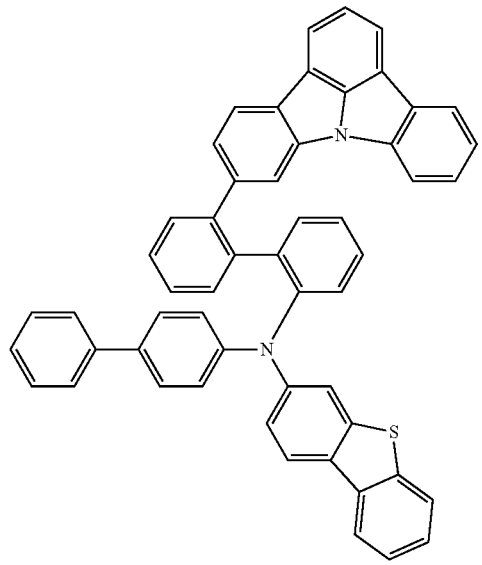
1-30
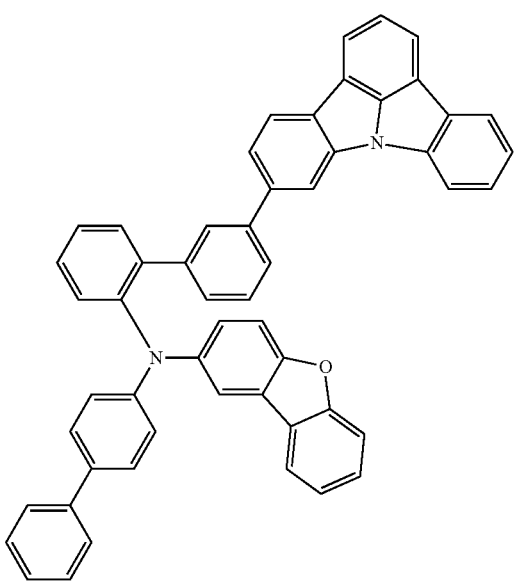
1-31
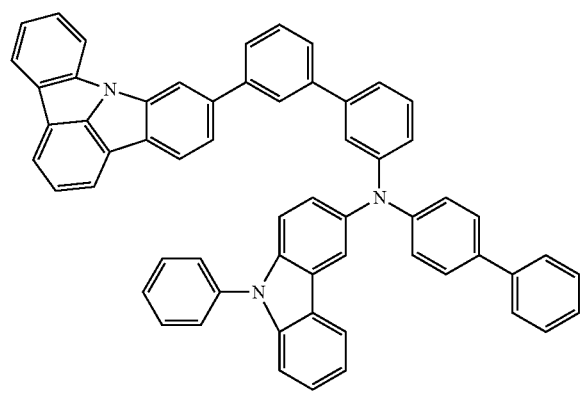
1-32
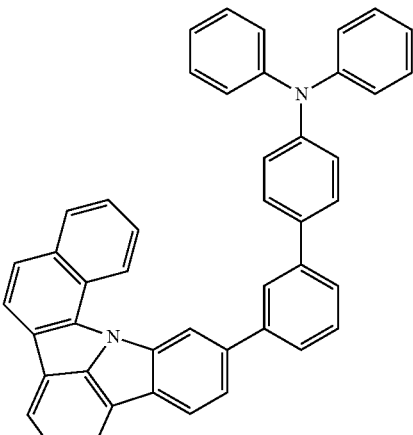
1-33
1-34
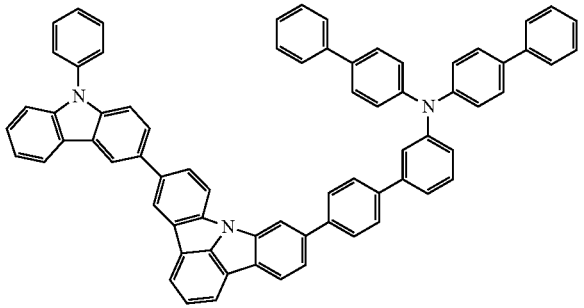

1-35

1-36

2-1

2-2

2-3

2-4

2-5

2-6

-continued
2-7
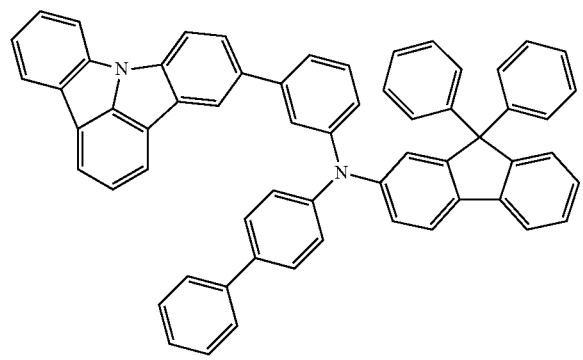
2-8
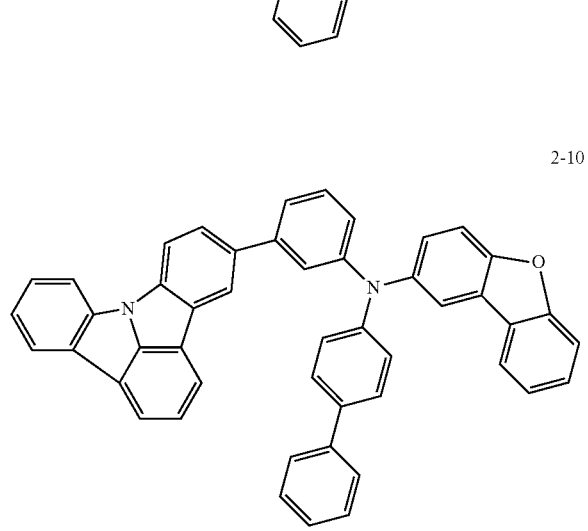
2-11
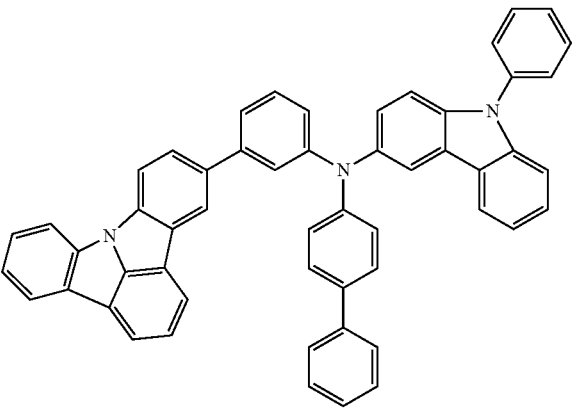
2-12
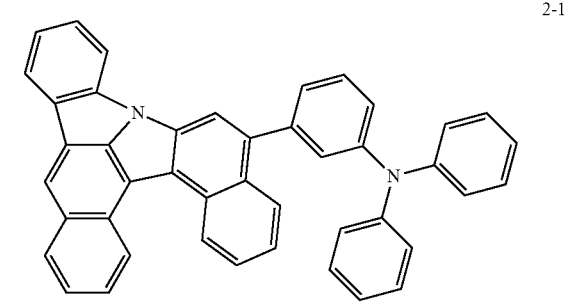
2-9
2-10
2-13
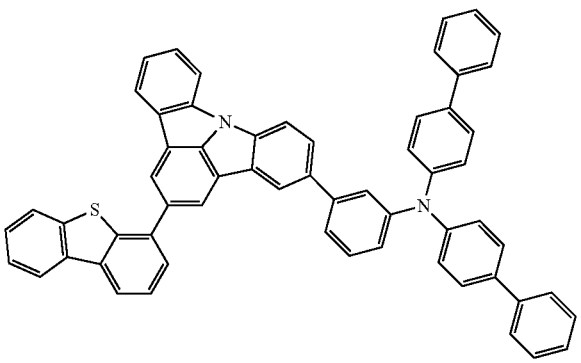
2-14
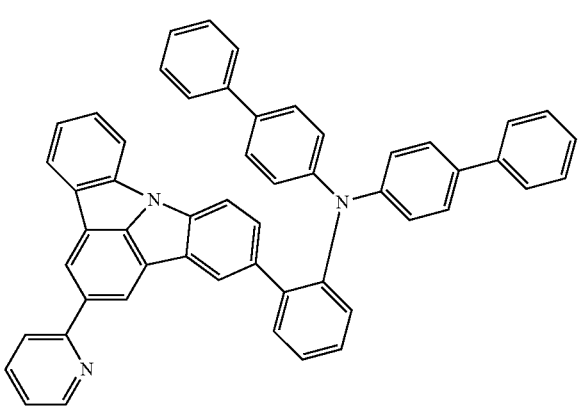

2-15
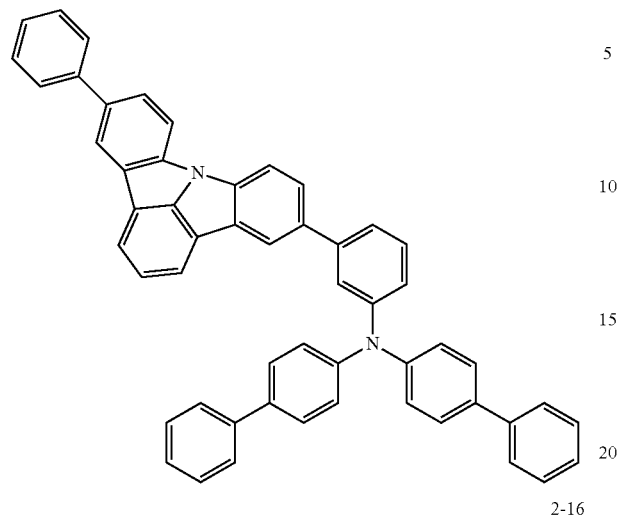
2-16
2-17
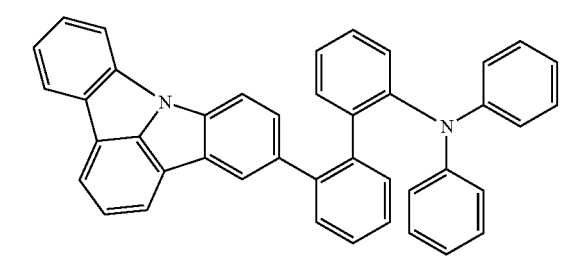
2-18
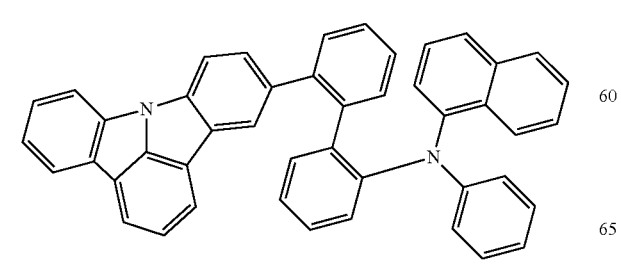
2-19
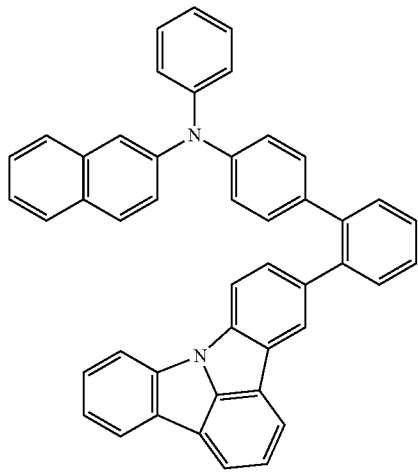
2-20
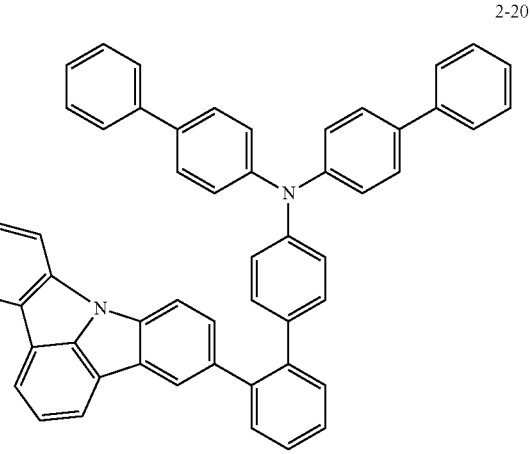
2-21

2-22
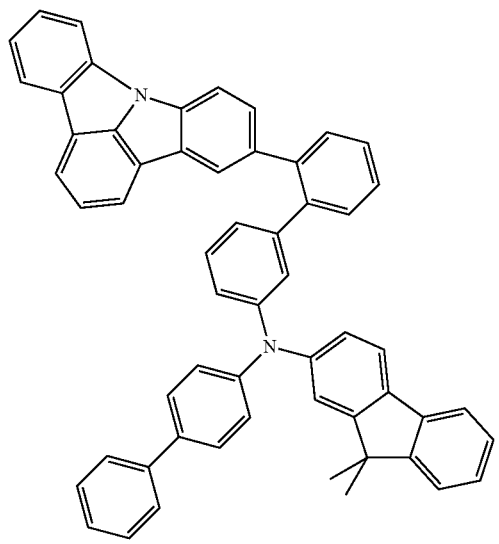
2-25
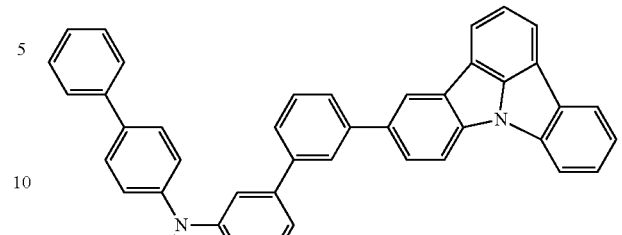
2-23
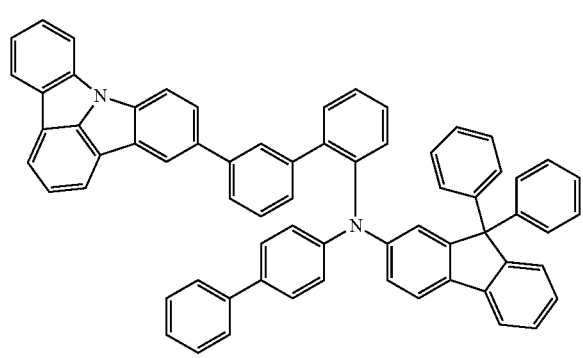
2-26
2-24
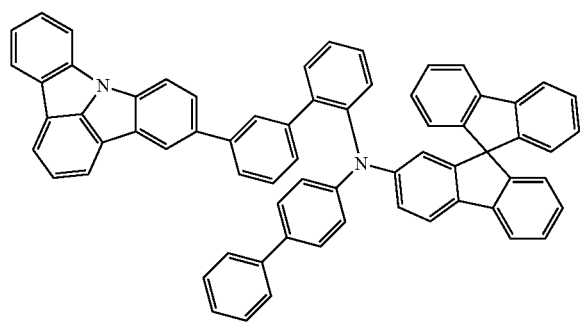
2-27
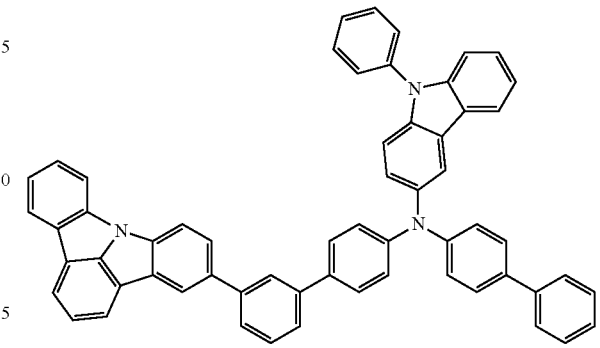

2-28
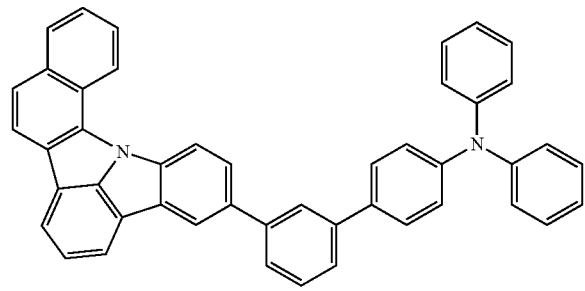
2-32
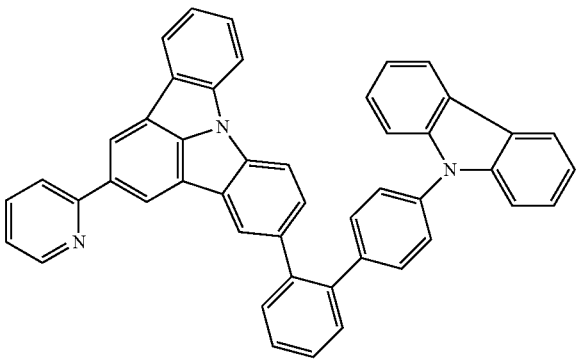
2-29
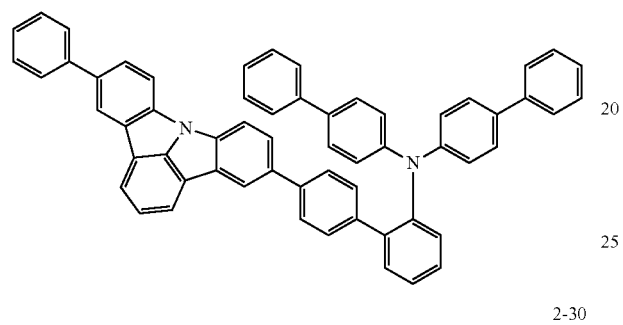
2-33
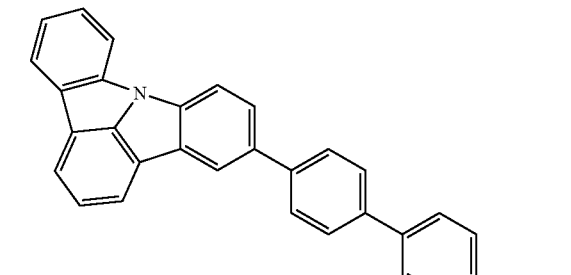
2-30
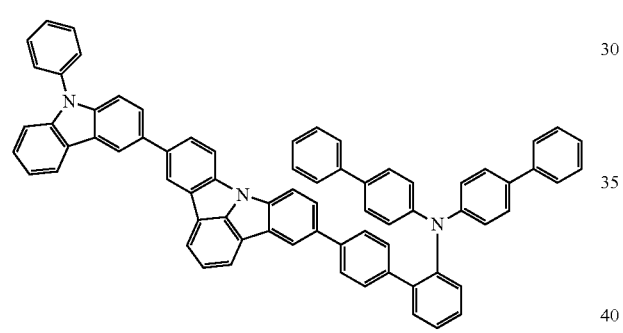
2-34
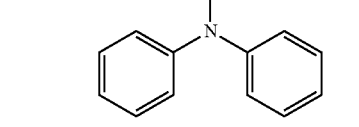
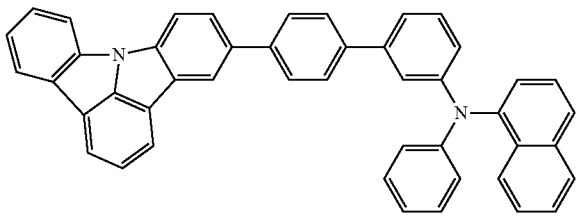
2-31
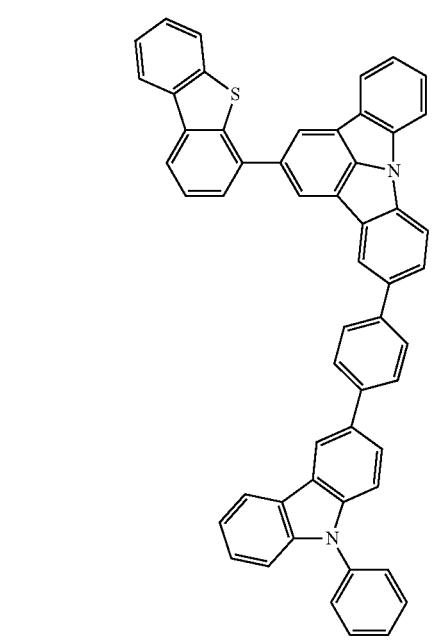
2-35
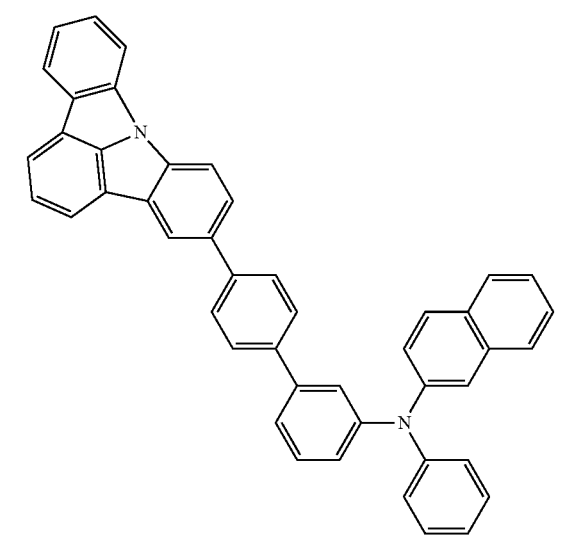

2-36

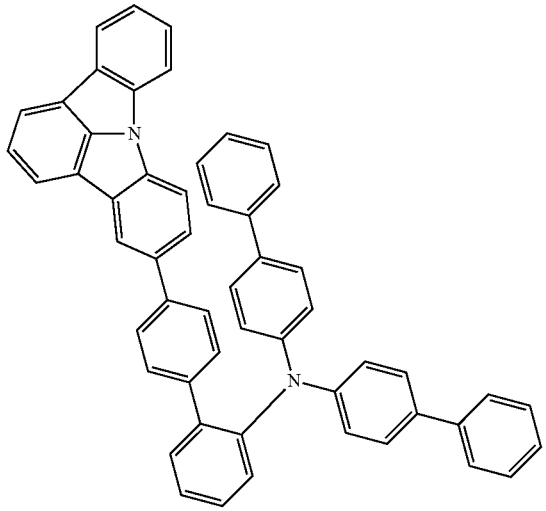

Referring to the FIGURE, the organic electric element (100) according to the present invention includes a first electrode(120) and a second electrode(180) formed on a substrate(110), and an organic material layer between the first electrode(120) and the second electrode(180), which contains the compound represented by Formula 1. Here, the first electrode(120) may be an anode (positive electrode), and the second electrode(180) may be a cathode (negative electrode). In the case of an inverted organic electric element, the first electrode may be a cathode, and the second electrode may be an anode.

The organic material layer may include a hole injection layer(130), a hole transport layer(140), an emitting layer (150), an electron transport layer(160), and an electron injection layer(170) formed in sequence on the first electrode(120). Here, the remaining layers except the emitting layer(150) may not be formed. The organic material layer may further include a hole blocking layer, an electron blocking layer, an emitting auxiliary layer(151), a buffer layer(141), etc., and the electron transport layer(160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interface property, etc.) of each organic material layer is achieved, a long life span and high efficiency can be achieved at the same time.

The organic electric element according to an embodiment of the present invention may be manufactured using a PVD (physical vapor deposition) method. For example, the organic electric element may be manufactured by depositing a metal or a conductive metal oxide or a mixture thereof on the substrate(110) to form the anode(120), forming the organic material layer including the hole injection layer (130), the hole transport layer(140), the emitting layer(150), the electron transport layer(160), and the electron injection layer(170) thereon, and then depositing a material, which can be used as the cathode(180), thereon.

Accordingly, the present invention provides the organic electric element comprising a first electrode; a second electrode; and an organic material layer disposed between the first electrode and the second electrode, wherein the organic material layer contains a compound included in the Formula (1).

In addition, the present invention may further include a light efficiency enhancing layer formed on at least one of the opposite side to the organic material layer among one side of the first electrode, or one of the opposite side to the organic material layer among one side of the second electrode.

In the present invention, the organic material layer is formed by any one of a spin coating process, a nozzle printing process, an inkjet printing process, a slot coating process, a dip coating process or a roll-to-roll process, wherein the organic material layer contains the compound as an electron transporting material.

In another specific examples of the invention, the present invention provides the organic electric element characterized in that the mixture of the same or different kinds of compounds represented Formula (1) is used in the organic material layer.

The present invention also provides a composition for a hole transport layer comprising a compound represented by Formula (1), and provides an organic electric element including the hole transport layer.

The present invention also provides a composition for an emitting auxiliary layer composition comprising a compound represented by Formula (1), and provides the organic electric element including the emitting auxiliary layer.

Accordingly, the present invention provides an organic electric element device comprising a hole transport layer and an emitting auxiliary layer containing a compound represented by Formula (1), and in another aspect, provides an organic electric element comprising a hole transport layer or an emitting auxiliary layer containing a compound represented by Formula (1).

The present invention also provides an electronic device including a display device including the organic electric element; and a control part driving the display apparatus.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, synthesis examples of the compound represented by Formula (1) according to the present invention and preparation examples of the organic electric element will be described in detail by way of example, but are not limited to the following examples of the invention.

Synthesis Example

The final product represented by Formula (1) according to the present invention is prepared by reacting Sub 1 or Sub 2 with Sub 3 as shown in Reaction Scheme 1 below.

<Reaction Scheme 1>
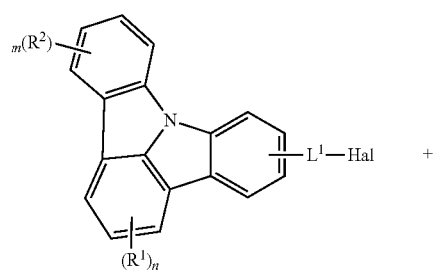
*Hal = halogen (F, Cl, Br, I)
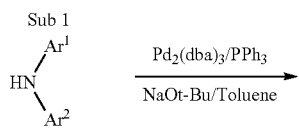
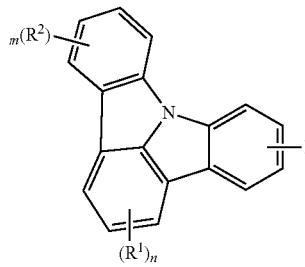
Final Products
Synthesis Examples of Sub 1
Sub 1 of Reaction Scheme 1 can be synthesized according to, but is not limited thereto, the reaction path of the following Reaction Scheme 2.
<Reaction Scheme 2>
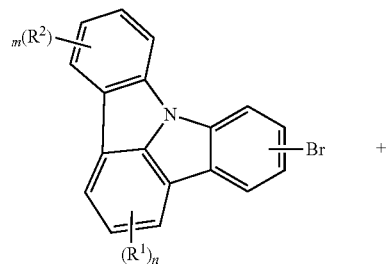
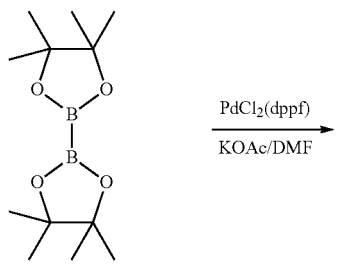
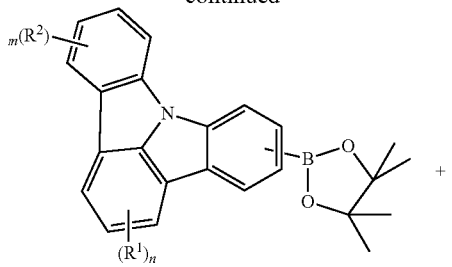
Sub 1-2
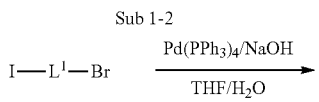
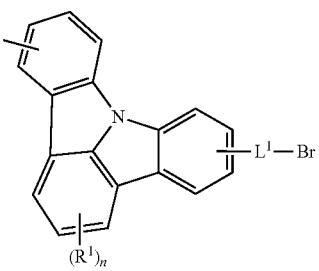
Sub 1
L is not a single bond.
Synthesis Examples of Sub 1(1)
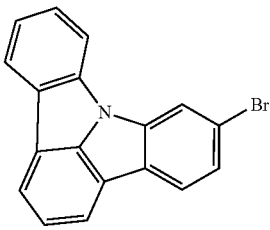
Sub 1-1-1
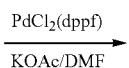
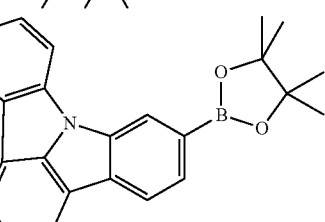
Sub 1-2-1

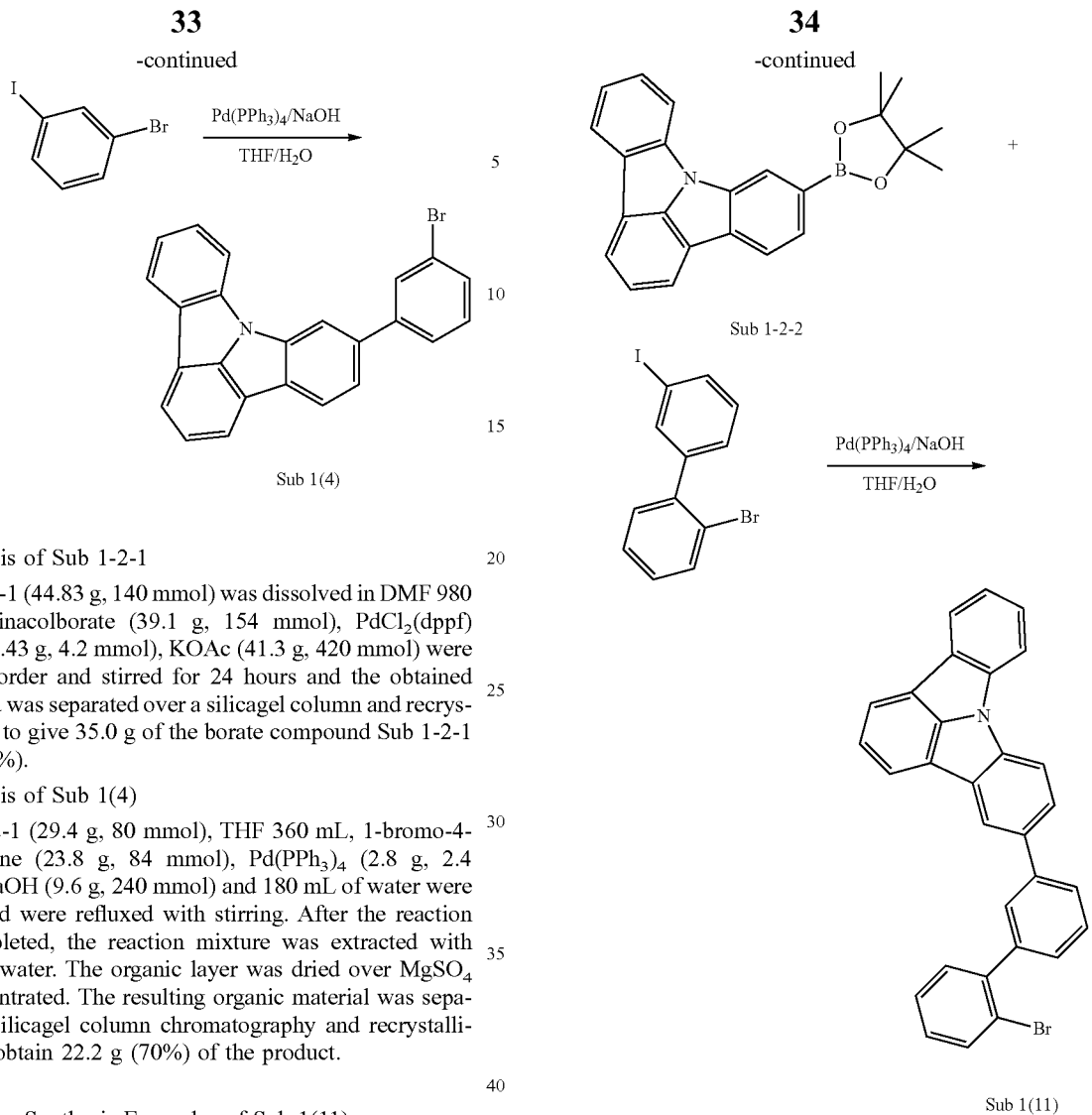

Synthesis of Sub 1-2-1

Sub 1-1-1 (44.83 g, 140 mmol) was dissolved in DMF 980 mL, Bispinacolborate (39.1 g, 154 mmol), PdCl$_2$(dppf) catalyst (3.43 g, 4.2 mmol), KOAc (41.3 g, 420 mmol) were added in order and stirred for 24 hours and the obtained compound was separated over a silicagel column and recrystallization to give 35.0 g of the borate compound Sub 1-2-1 (yield: 68%).

Synthesis of Sub 1(4)

Sub 1-2-1 (29.4 g, 80 mmol), THF 360 mL, 1-bromo-4-iodobenzene (23.8 g, 84 mmol), Pd(PPh$_3$)$_4$ (2.8 g, 2.4 mmol), NaOH (9.6 g, 240 mmol) and 180 mL of water were mixed, and were refluxed with stirring. After the reaction was completed, the reaction mixture was extracted with ether and water. The organic layer was dried over MgSO$_4$ and concentrated. The resulting organic material was separated by silicagel column chromatography and recrystallization to obtain 22.2 g (70%) of the product.

Synthesis Examples of Sub 1(11)

Synthesis of Sub 1-2-2

Sub 1-1-2 (44.83 g, 140 mmol) was dissolved in 980 mL of DMF, and 20.3 g (69%) of Sub 1-2-2 was obtained in the same manner as Sub 1-2-1.

Synthesis of Sub 1(11)

Sub 1-2-2 (29.4 g, 80 mmol), THF (360 mL), and 2-bromo-3'-iodo-1,1'-biphenyl(30.2 g, 84 mmol) were carried out in the same manner as in Sub 1(1) to give 24.6 g of the product (65%).

Examples of Sub 1 include, but are not limited thereto, the following compounds.

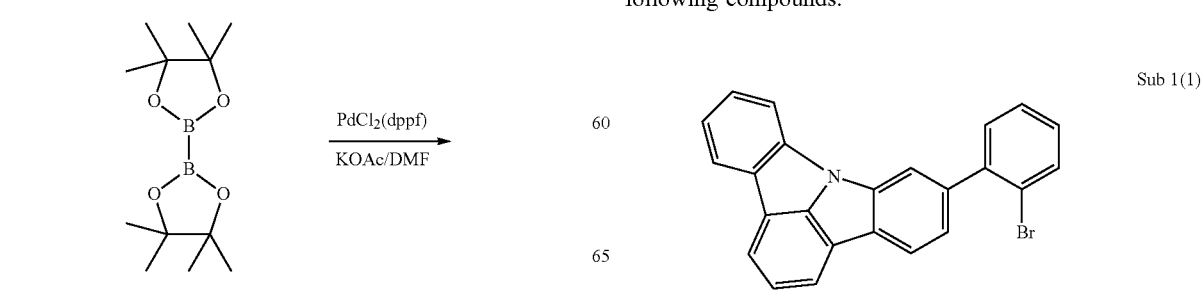

Sub 1(2)
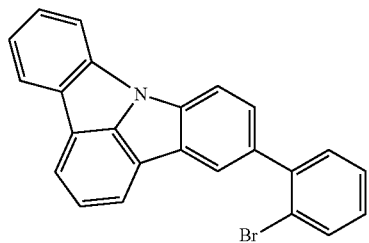
Sub 1(3)
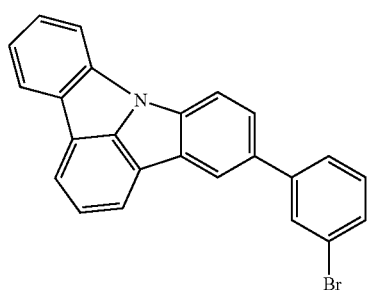
Sub 1(4)
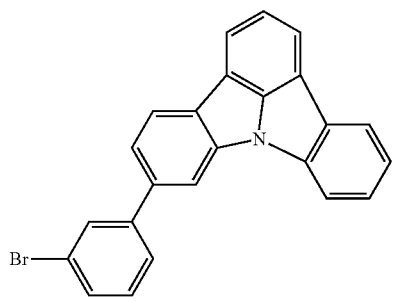
Sub 1(5)
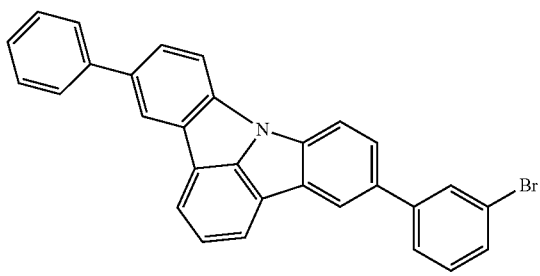
Sub 1(6)
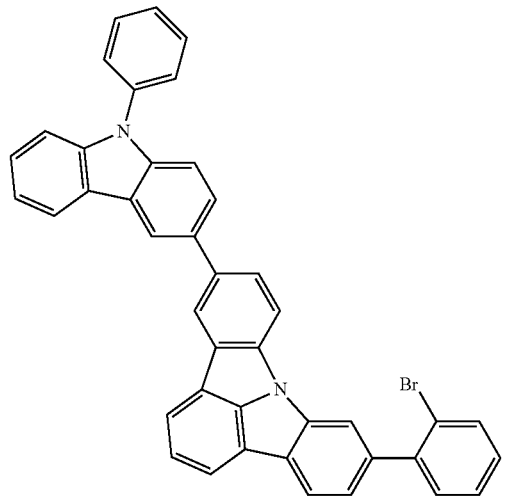
Sub 1(7)
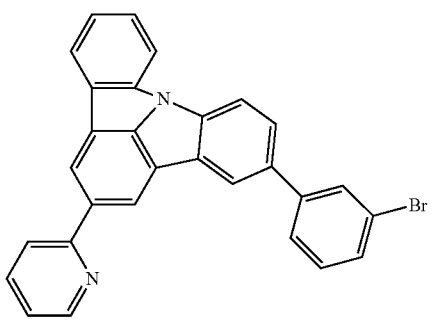
Sub 1(8)
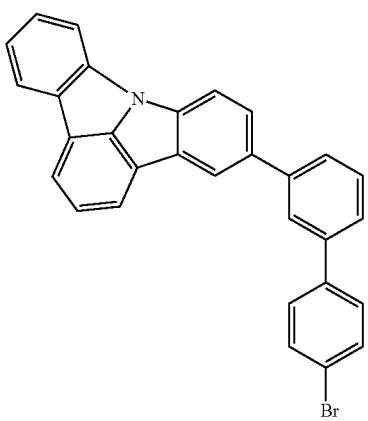

Sub 1(9)

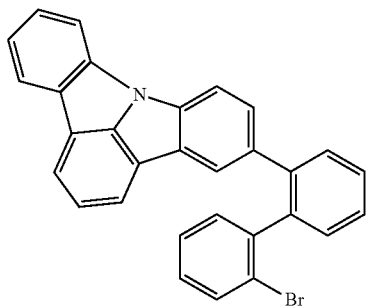

Sub 1(10)

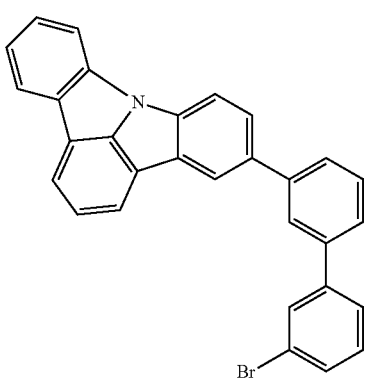

Sub 1(11)

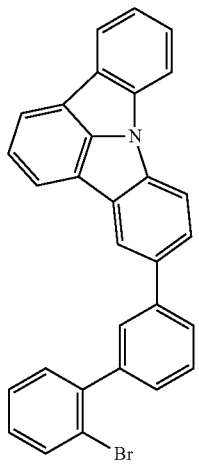

Sub 1(12)

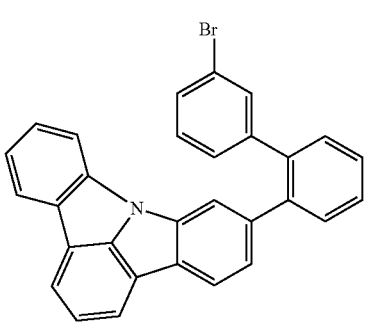

TABLE 1

| compound | FD-MS | compound | FD-MS |
|---|---|---|---|
| Sub 1(1) | m/z = 395.03($C_{24}H_{14}BrN$ = 396.28) | Sub 1(2) | m/z = 395.03($C_{24}H_{14}BrN$ = 396.28) |
| Sub 1(3) | m/z = 395.03($C_{24}H_{14}BrN$ = 396.28) | Sub 1(4) | m/z = 395.03($C_{24}H_{14}BrN$ = 396.28) |
| Sub 1(5) | m/z = 471.06($C_{30}H_{18}BrN$ = 472.37) | Sub 1(6) | m/z = 636.12($C_{42}H_{25}BrN_2$ = 637.57) |
| Sub 1(7) | m/z = 472.06($C_{29}H_{17}BrN_2$ = 473.36) | Sub 1(8) | m/z = 471.06($C_{30}H_{18}BrN$ = 472.37) |
| Sub 1(9) | m/z = 471.06($C_{30}H_{18}BrN$ = 472.37) | Sub 1(10) | m/z = 471.06($C_{30}H_{18}BrN$ = 472.37) |
| Sub 1(11) | m/z = 471.06($C_{30}H_{18}BrN$ = 472.37) | Sub 1(12) | m/z = 471.06($C_{30}H_{18}BrN$ = 472.37) |

Synthesis Examples of Sub 2

Sub 2 of Reaction Scheme 1 can be synthesized according to, but is not limited thereto, the reaction path of the following Reaction Scheme 3.

<Reaction Scheme 3>

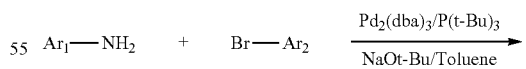

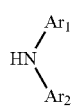

Sub 2

Synthesis Example of Sub 2-28

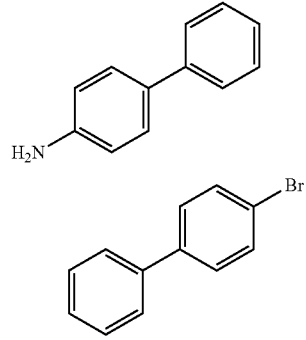

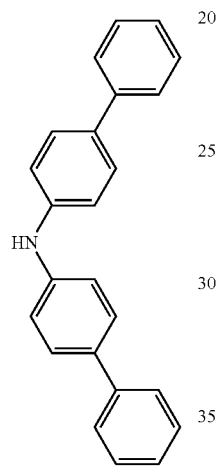

Sub 2-28

4-bromo-1,1'-biphenyl (5.6 g, 24 mmol) was dissolved in toluene, [1,1'-biphenyl]-4-amine (3.4 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, and the mixture was refluxed with stirring at 100° C. for 24 hours. After the reaction was completed, the reaction mixture was extracted with ether and water. The organic layer was dried over MgSO$_4$ and concentrated. The resulting organic material was separated by silicagel column chromatography and recrystallization to obtain 6.2 g of the final product. (yield: 80%)

Examples of Sub 2 include, but are not limited thereto, the following compounds.

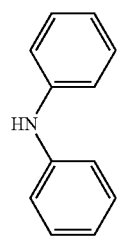

Sub 2-1

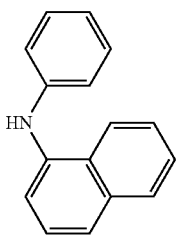

Sub 2-2

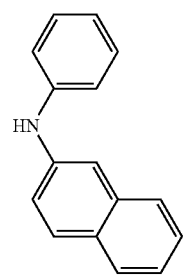

Sub 2-3

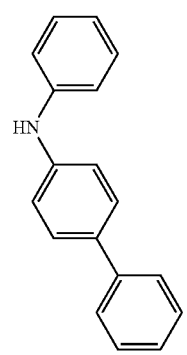

Sub 2-4

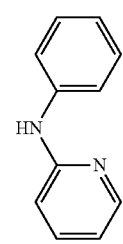

Sub 2-5

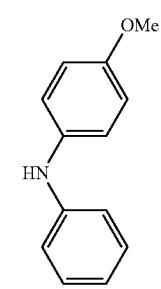

Sub 2-6

-continued
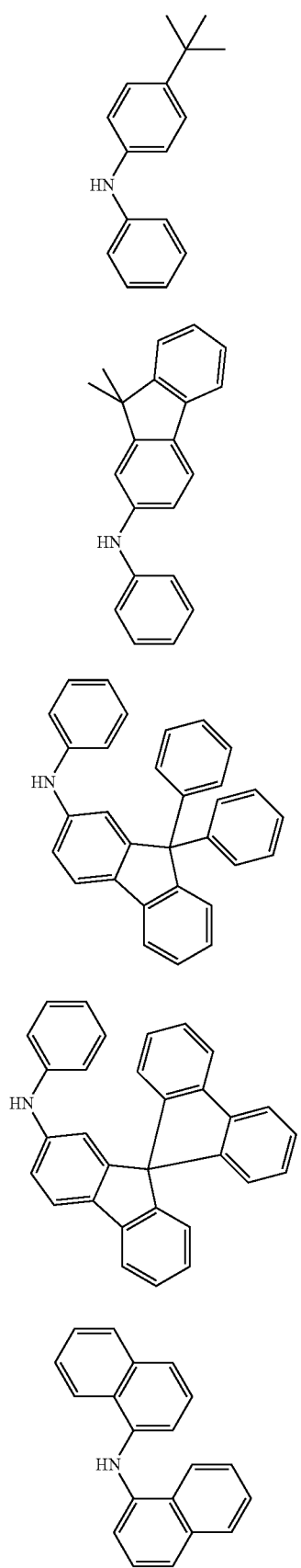
Sub 2-7
Sub 2-8
Sub 2-9
Sub 2-10
Sub 2-11
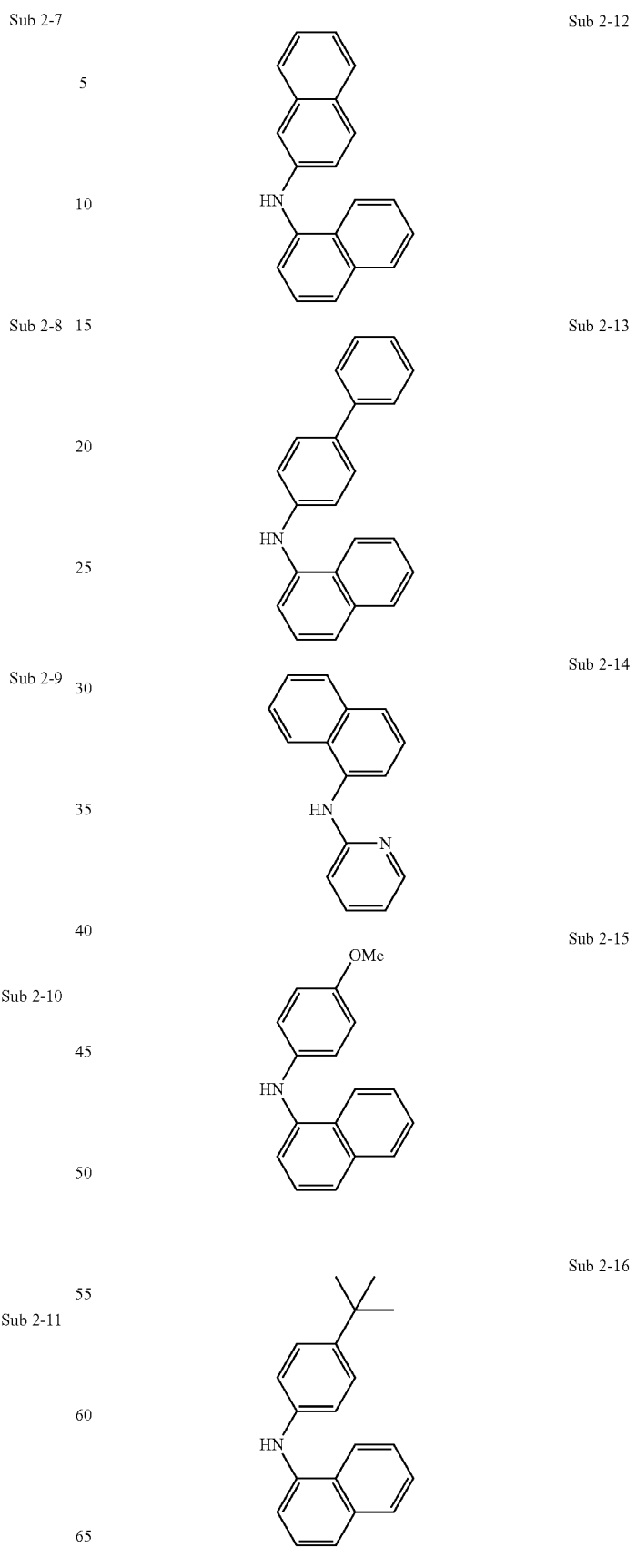
Sub 2-12
Sub 2-13
Sub 2-14
Sub 2-15
Sub 2-16

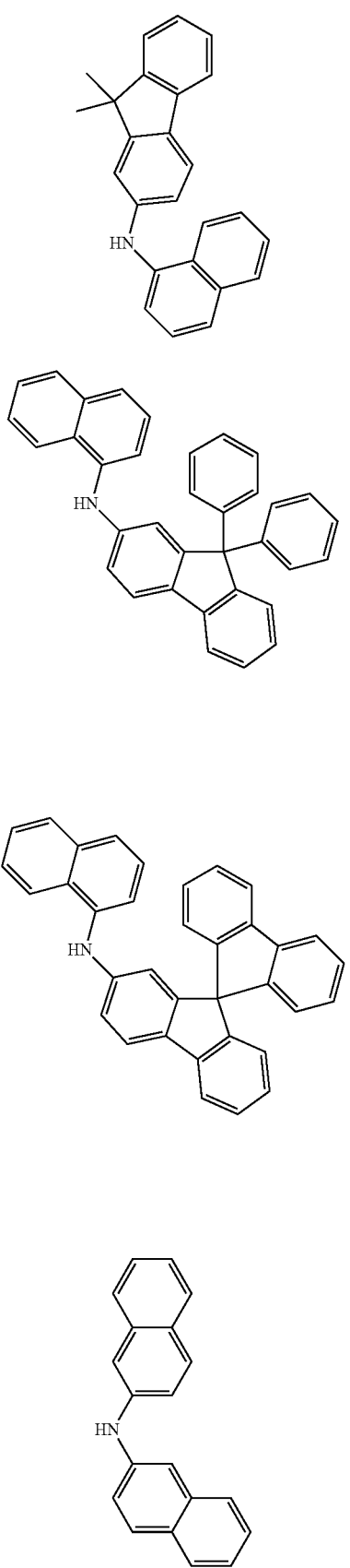
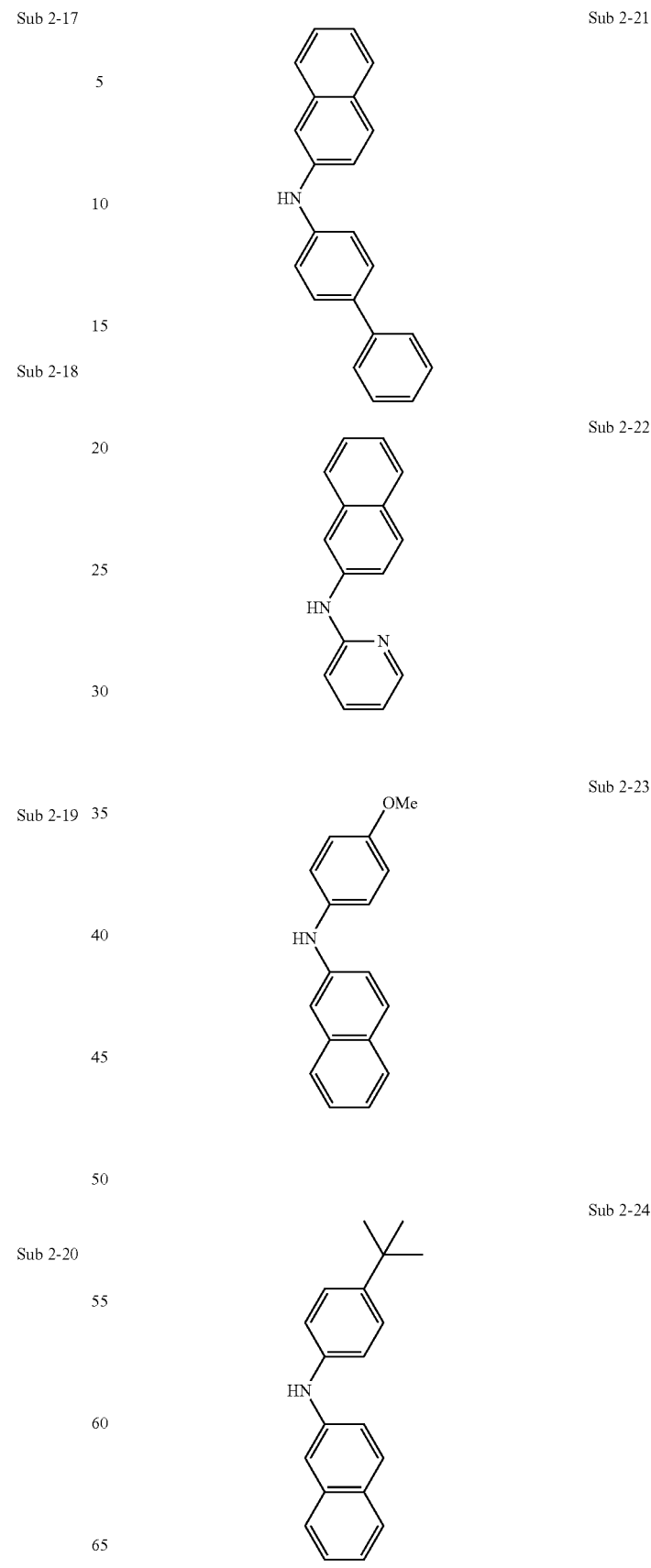

Sub 2-25
Sub 2-26
Sub 2-27
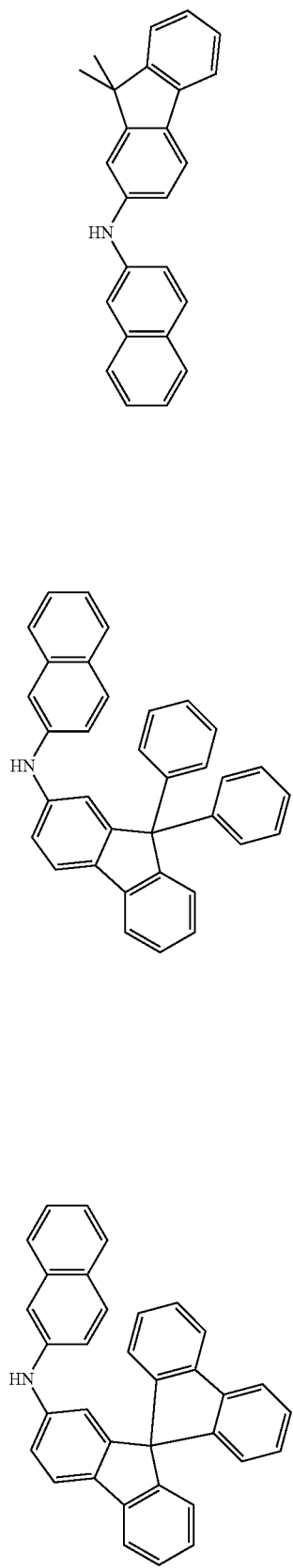
Sub 2-28
Sub 2-29
Sub 2-30
Sub 2-31
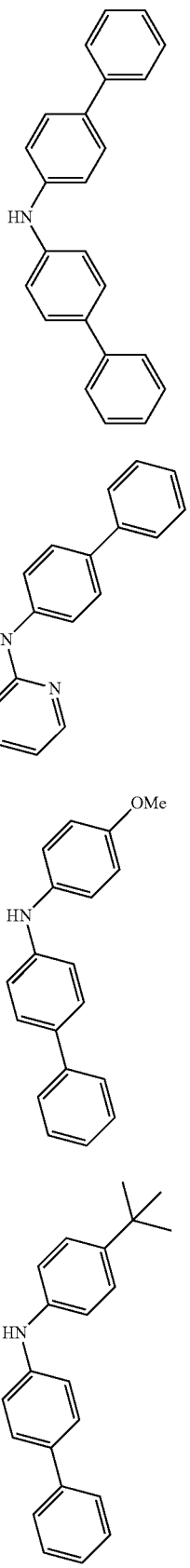

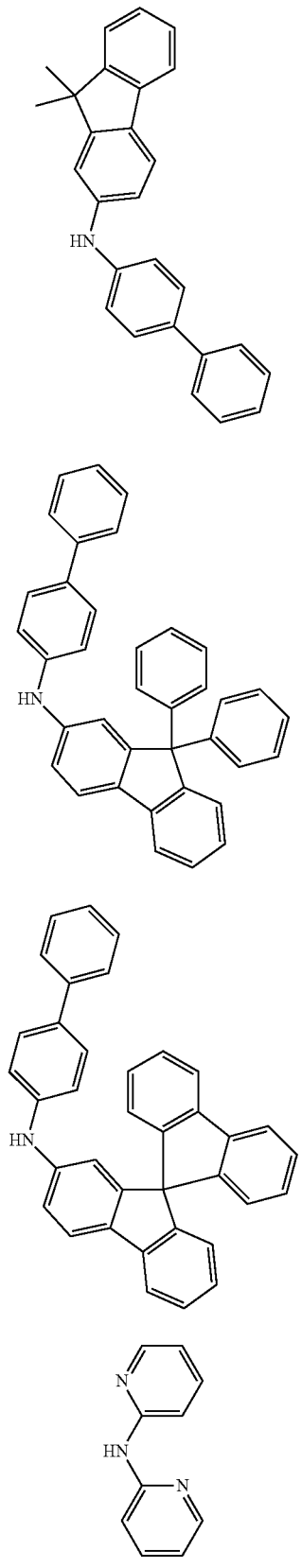

Sub 2-41
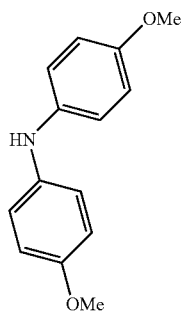
Sub 2-42
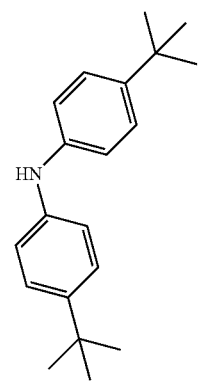
Sub 2-43
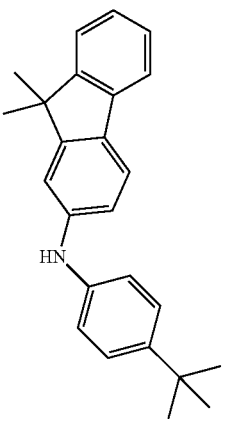
Sub 2-44
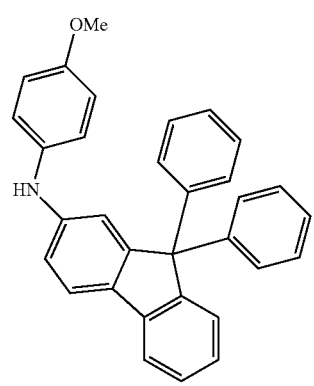
Sub 2-45
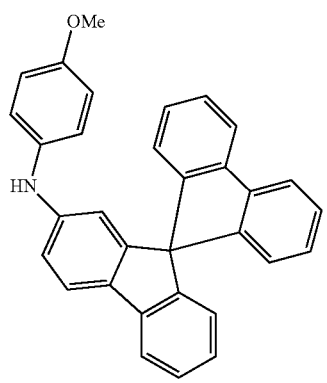
Sub 2-46
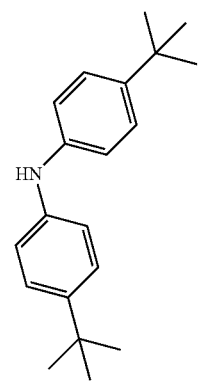
Sub 2-47
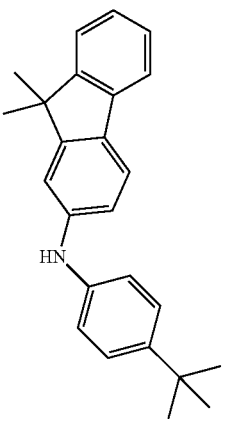
Sub 2-48
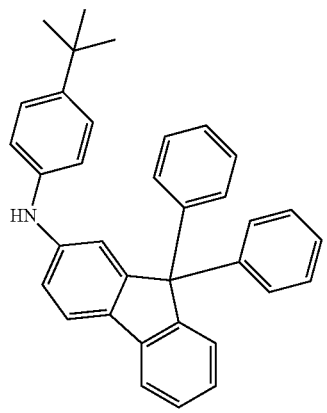

Sub 2-49
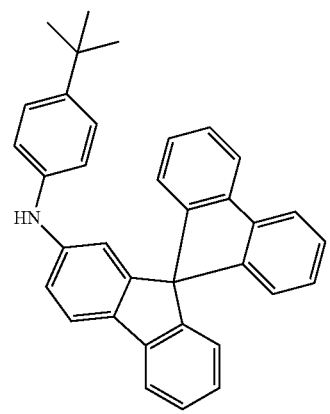
Sub 2-50
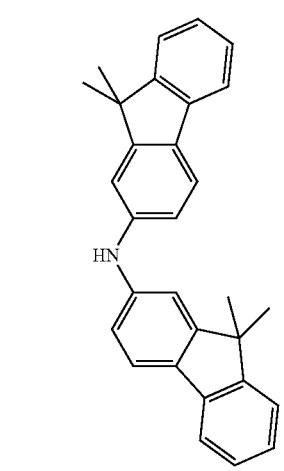
Sub 2-51
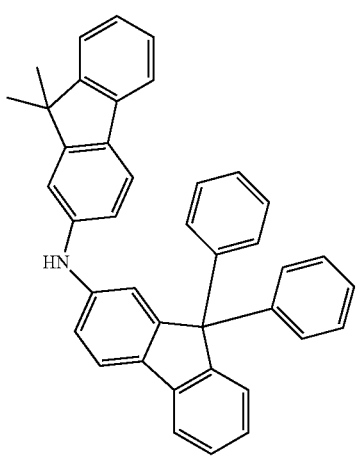
Sub 2-52
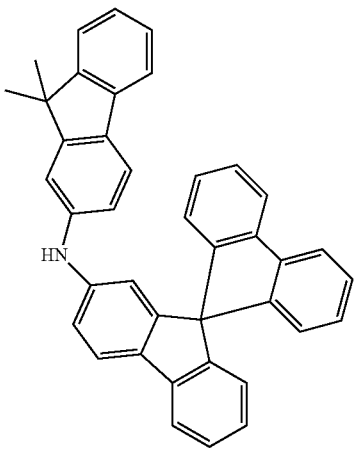
Sub 2-53
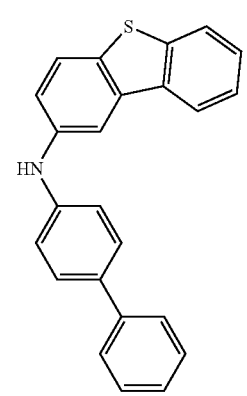
Sub 2-54
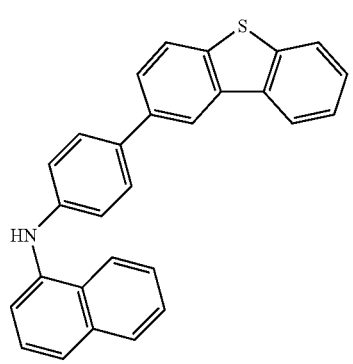
Sub 2-55
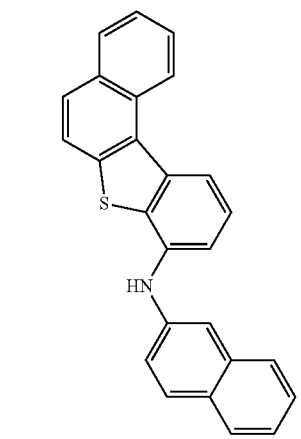

Sub 2-56
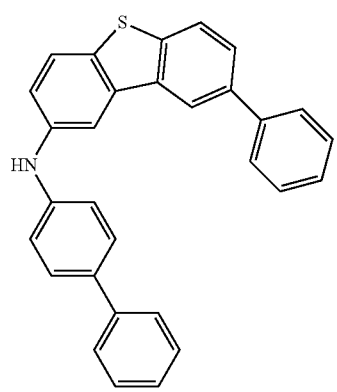
Sub 2-57
Sub 2-58
Sub 2-59
Sub 2-60
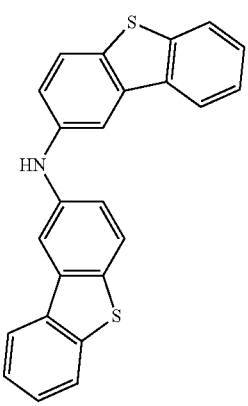
Sub 2-61
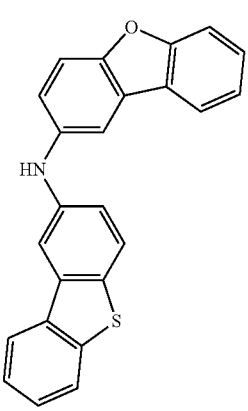
Sub 2-62
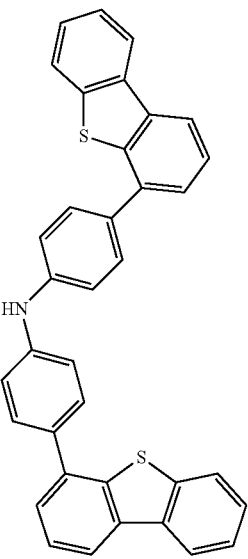

Sub 2-63

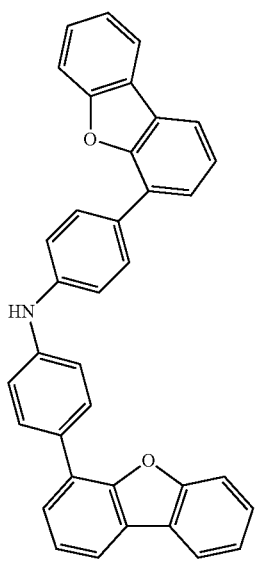

Sub 2-64

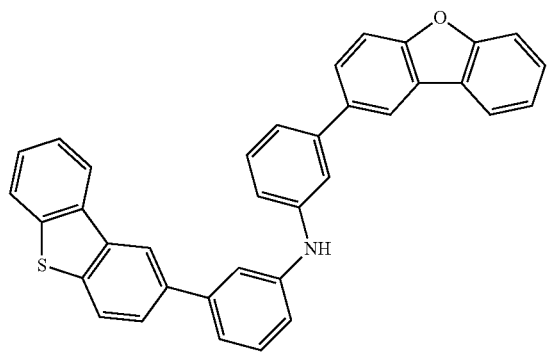

TABLE 2

| compound | FD-MS | compound | FD-MS |
| --- | --- | --- | --- |
| Sub 2-1 | m/z = 169.09($C_{12}H_{11}N$ = 169.22) | Sub 2-2 | m/z = 219.10($C_{16}H_{13}N$ = 219.28) |
| Sub 2-3 | m/z = 219.10($C_{16}H_{13}N$ = 219.28) | Sub 2-4 | m/z = 245.12($C_{18}H_{15}N$ = 245.32) |
| Sub 2-5 | m/z = 170.08($C_{11}H_{10}N_2$ = 170.21) | Sub 2-6 | m/z = 199.10($C_{10}H_{13}NO$ = 199.25) |
| Sub 2-7 | m/z = 225.15($C_{16}H_{19}N$ = 225.33) | Sub 2-8 | m/z = 285.15($C_{21}H_{19}N$ = 285.38) |
| Sub 2-9 | m/z = 409.18($C_{31}H_{23}N$ = 409.52) | Sub 2-10 | m/z = 407.17($C_{31}H_{21}N$ = 407.51) |
| Sub 2-11 | m/z = 269.12($C_{20}H_{15}N$ = 269.34) | Sub 2-12 | m/z = 269.12($C_{20}H_{15}N$ = 269.34) |
| Sub 2-13 | m/z = 295.14($C_{22}H_{17}N$ = 295.38) | Sub 2-14 | m/z = 220.10($C_{15}H_{12}N_2$ = 220.27) |
| Sub 2-15 | m/z = 249.12($C_{17}H_{12}NO$ = 249.31) | Sub 2-16 | m/z = 275.17($C_{20}H_{21}N$ = 275.39) |
| Sub 2-17 | m/z = 335.17($C_{25}H_{21}N$ = 335.44) | Sub 2-18 | m/z = 459.20($C_{35}H_{25}N$ = 459.58) |
| Sub 2-19 | m/z = 457.18($C_{35}H_{23}N$ = 457.56) | Sub 2-20 | m/z = 269.12($C_{20}H_{15}N$ = 269.34) |
| Sub 2-21 | m/z = 295.14($C_{22}H_{17}N$ = 295.38) | Sub 2-22 | m/z = 220.10($C_{15}H_{12}N_2$ = 220.27) |
| Sub 2-23 | m/z = 249.12($C_{17}H_{15}NO$ = 249.31) | Sub 2-24 | m/z = 275.17($C_{20}H_{21}N$ = 275.39) |
| Sub 2-25 | m/z = 335.17($C_{25}H_{21}N$ = 335.44) | Sub 2-26 | m/z = 459.20($C_{35}H_{25}N$ = 459.58) |
| Sub 2-27 | m/z = 457.18($C_{35}H_{23}N$ = 457.56) | Sub 2-28 | m/z = 321.15($C_{24}H_{19}N$ = 321.41) |
| Sub 2-29 | m/z = 246.12($C_{17}H_{14}N_2$ = 246.31) | Sub 2-30 | m/z = 275.13($C_{19}H_{17}NO$ = 275.34) |
| Sub 2-31 | m/z = 301.18($C_{22}H_{23}N$ = 301.42) | Sub 2-32 | m/z = 361.18($C_{27}H_{23}N$ = 361.48) |
| Sub 2-33 | m/z = 485.21($C_{37}H_{27}N$ = 485.62) | Sub 2-34 | m/z = 483.20($C_{37}H_{25}N$ = 483.60) |
| Sub 2-35 | m/z = 171.08($C_{10}H_{09}N_3$ = 171.20) | Sub 2-36 | m/z = 200.09($C_{12}H_{12}N_2O$ = 200.24) |
| Sub 2-37 | m/z = 226.15($C_{15}H_{18}N_2$ = 226.32) | Sub 2-38 | m/z = 286.15($C_{20}H_{18}N_2$ = 286.37) |
| Sub 2-39 | m/z = 410.18($C_{30}H_{22}N_2$ = 410.51) | Sub 2-40 | m/z = 408.16($C_{30}H_{20}N_2$ = 408.49) |
| Sub 2-41 | m/z = 229.11($C_{14}H_{15}NO_2$ = 229.27) | Sub 2-42 | m/z = 255.16($C_{17}H_{21}NO$ = 255.35) |
| Sub 2-43 | m/z = 315.16($C_{22}H_{21}NO$ = 315.41) | Sub 2-44 | m/z = 439.19($C_{32}H_{25}NO$ = 439.55) |
| Sub 2-45 | m/z = 437.18($C_{32}H_{23}NO$ = 437.53) | Sub 2-46 | m/z = 281.21($C_{20}H_{27}N$ = 281.44) |
| Sub 2-47 | m/z = 341.21($C_{25}H_{27}N$ = 341.49) | Sub 2-48 | m/z = 465.25($C_{35}H_{31}N$ = 465.63) |
| Sub 2-49 | m/z = 463.23($C_{35}H_{29}N$ = 463.61) | Sub 2-50 | m/z = 401.21($C_{30}H_{27}N$ = 401.54) |
| Sub 2-51 | m/z = 525.25($C_{40}H_{31}N$ = 525.68) | Sub 2-52 | m/z = 523.23($C_{40}H_{29}N$ = 523.66) |
| Sub 2-53 | m/z = 351.11($C_{24}H_{17}NS$ = 351.46) | Sub 2-54 | m/z = 401.12($C_{28}H_{19}NS$ = 401.52) |
| Sub 2-55 | m/z = 357.11($C_{26}H_{17}NS$ = 375.48) | Sub 2-56 | m/z = 427.14($C_{30}H_{21}NS$ = 427.56) |
| Sub 2-57 | m/z = 335.13($C_{24}H_{17}NO$ = 335.40) | Sub 2-58 | m/z = 335.13($C_{24}H_{17}NO$ = 335.40) |
| Sub 2-59 | m/z = 349.11($C_{24}H_{15}NO_2$ = 349.38) | Sub 2-60 | m/z = 381.06($C_{24}H_{15}NS_2$ = 381.51) |
| Sub 2-61 | m/z = 365.09($C_{24}H_{15}NOS$ = 365.45) | Sub 2-62 | m/z = 533.13($C_{36}H_{23}NS_2$ = 533.70) |
| Sub 2-63 | m/z = 501.17($C_{36}H_{23}NO_2$ = 501.57) | Sub 2-64 | m/z = 517.15($C_{36}H_{23}NOS$ = 349.38) |

Synthesis Example of Final Products

Synthesis Example of 1-5

Synthesis Example of 1-6

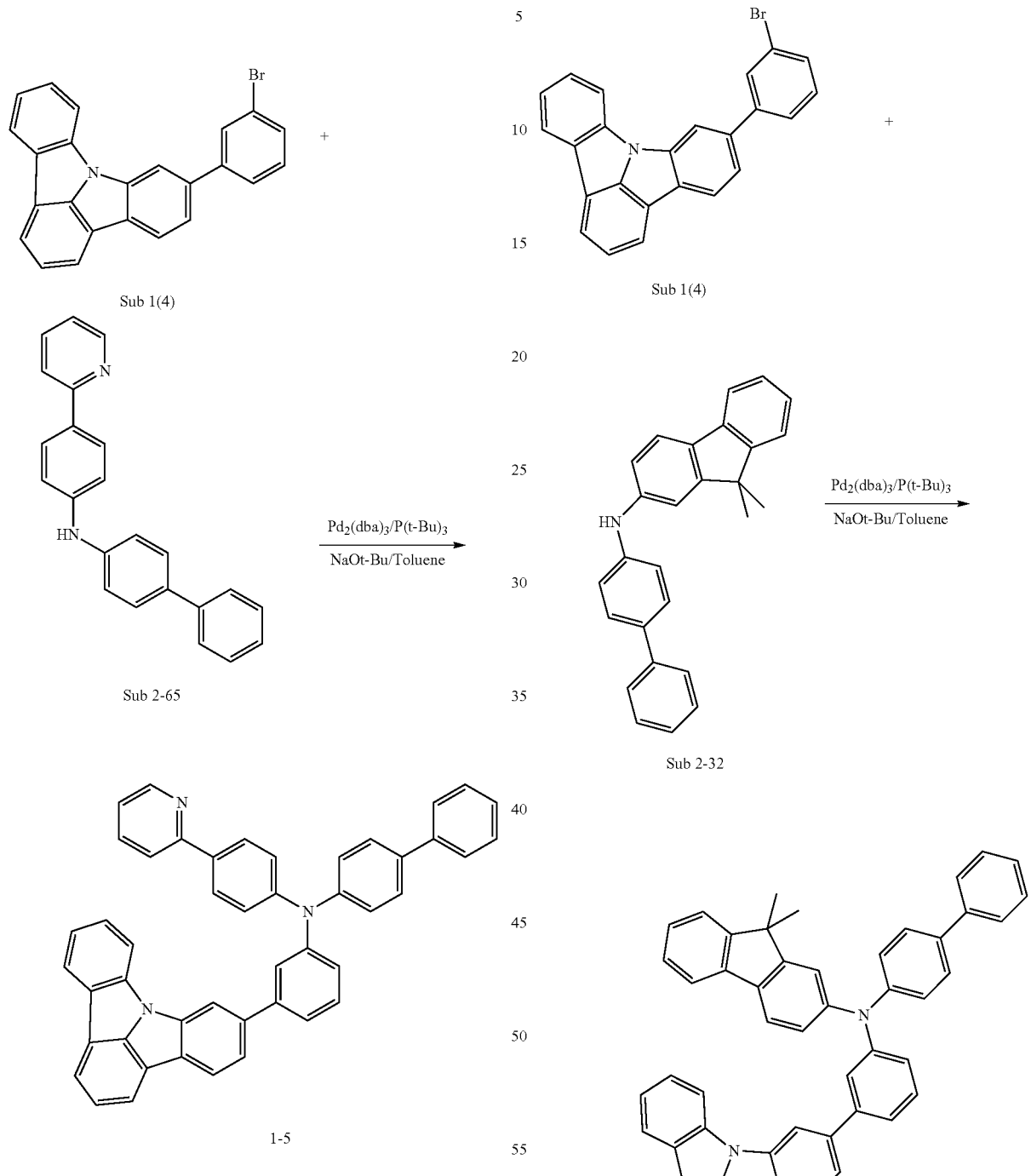

Sub 1(4)(9.5 g, 24 mmol) was dissolved in toluene, Sub 2-65 (6.5 g, 20 mmol), Pd$_2$(dba)$_3$ (0.5 g, 0.6 mmol), P(t-Bu)$_3$ (0.2 g, 2 mmol), NaOt-Bu (5.8 g, 60 mmol) and toluene (300 mL) were added, and the mixture was refluxed with stirring at 100° C. for 24 hours. After the reaction was completed, the reaction mixture was extracted with ether and water. The organic layer was dried over MgSO$_4$ and concentrated. The resulting organic material was separated by silicagel column chromatography and recrystallization to obtain 10.1 g of the final product. (yield:66%)

Sub 1(4)(9.5 g, 24 mmol) was dissolved in Toluene, and Sub 2-32 (7.2 g, 20 mmol) was added, the same procedure as described in the synthesis method of the 1-5 was carried out to obtain 11.0 g of the final product. (yield:68%).

Synthesis Example of 2-1

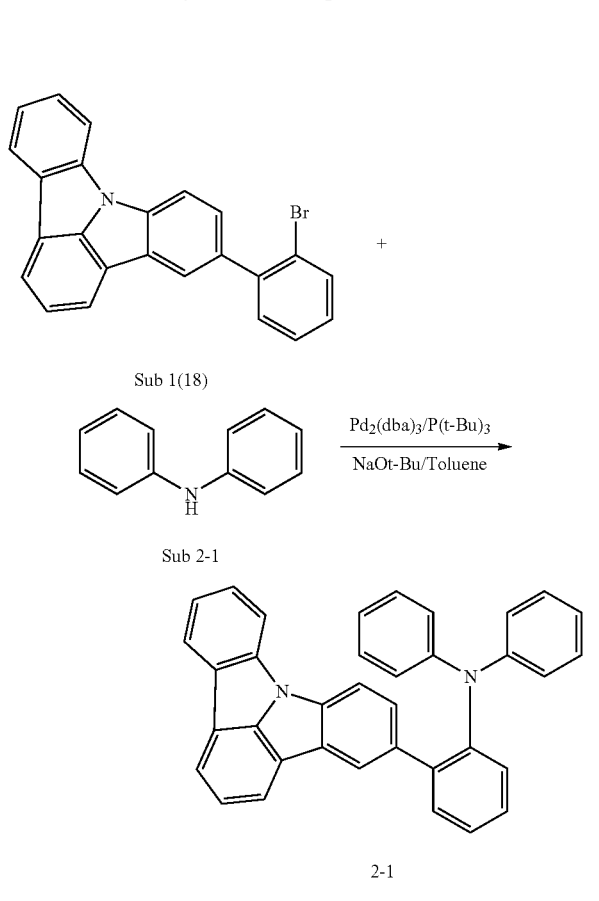

Sub 1(18)(9.5 g, 24 mmol) was dissolved in Toluene, and Sub 2-1 (7.2 g, 20 mmol) was added, the same procedure as described in the synthesis method of the 1-4 was carried out to obtain 7.4 g of the final product. (yield:64%).

Synthesis Example of 2-16

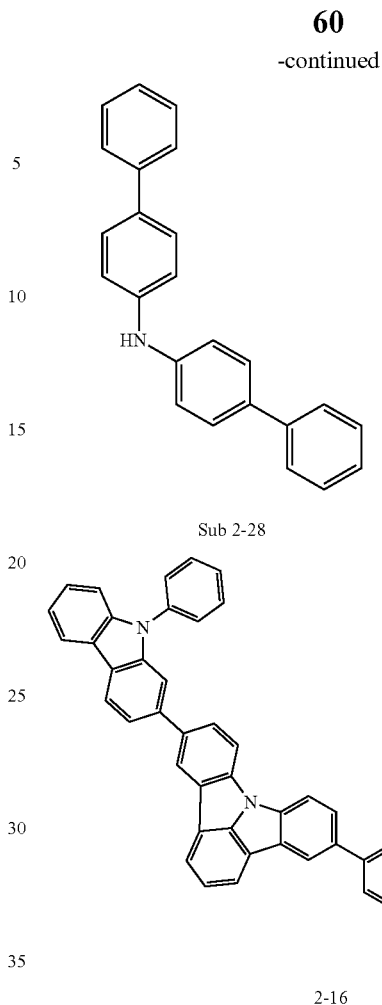

Sub 1(19)(15.3 g, 24 mmol) was dissolved in Toluene, and Sub 2-28 (6.5 g, 20 mmol) was added, the same procedure as described in the synthesis method of the 1-4 was carried out to obtain 13.9 g of the final product. (yield:66%).

Synthesis Example of 2-21

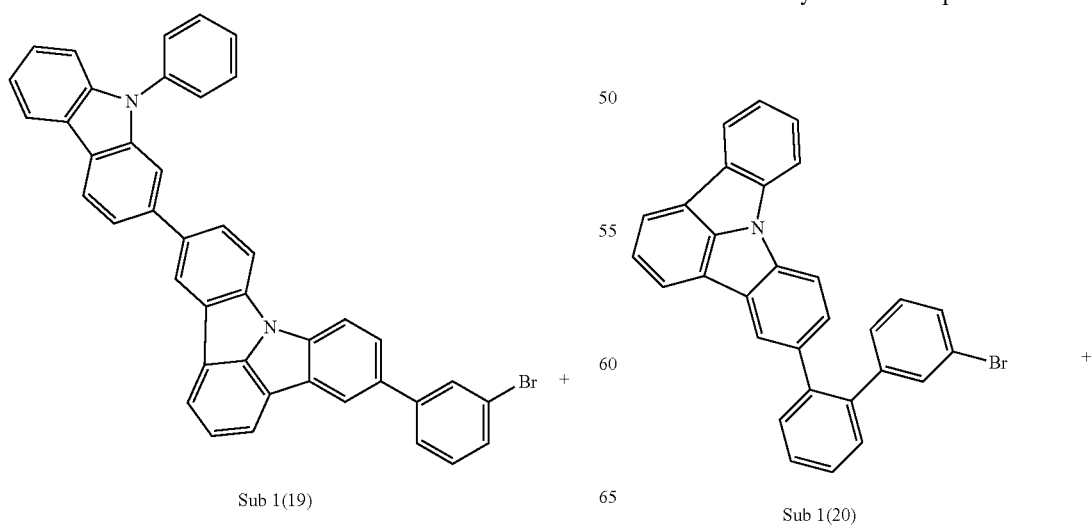

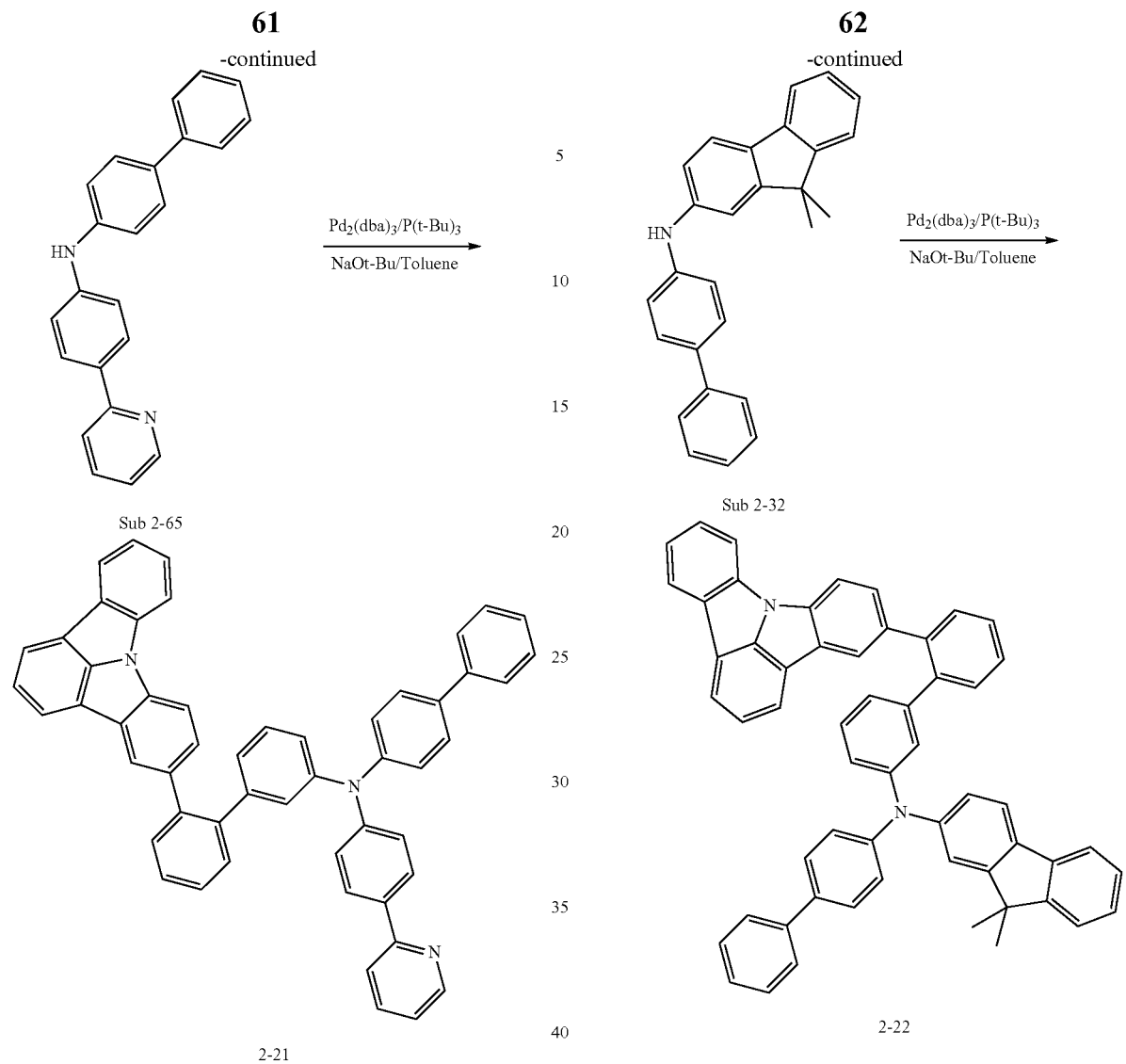

Sub 1(20)(11.3 g, 24 mmol) was dissolved in Toluene, and Sub 2-65 (6.5 g, 20 mmol) was added, the same procedure as described in the synthesis method of the 1-4 was carried out to obtain 11.1 g of the final product. (yield:65%).

Synthesis Example of 2-22

Sub 1(21)(11.3 g, 24 mmol) was dissolved in Toluene, and Sub 2-32 (7.2 g, 20 mmol) was added, the same procedure as described in the synthesis method of the 1-4 was carried out to obtain 12.1 g of the final product. (yield:679%)).

Synthesis Example of 2-33

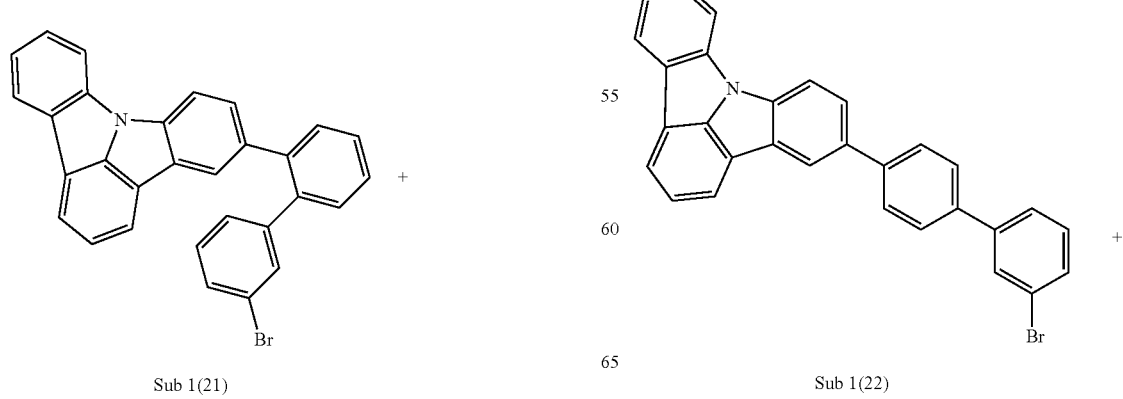

-continued

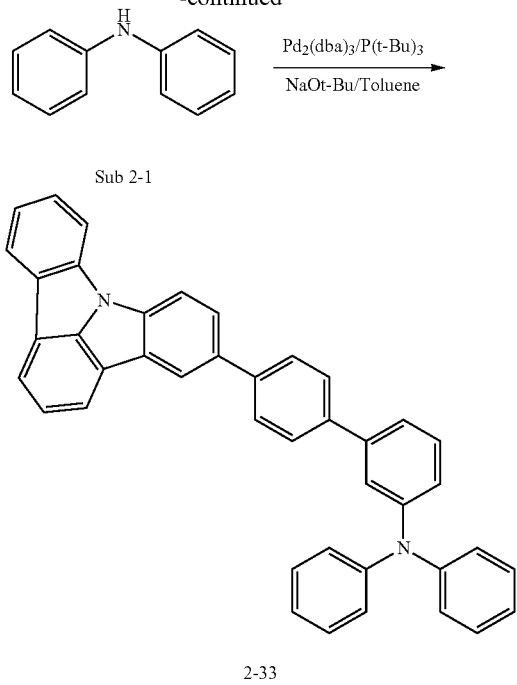

Sub 2-1

2-33

Sub 1(22) (11.3 g, 24 mmol) was dissolved in Toluene, and Sub 2-1 (3.4 g, 20 mmol) was added, the same procedure as described in the synthesis method of the 1-4 was carried out to obtain 9.3 g of the final product. (yield:69%).

Manufacture and Evaluation of Organic Electric Element

Example 1) Blue Organic Light Emitting Diode (Hole Transport Layer)

First, on an ITO layer(anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and on the hole transport layer, the compound 1-1 of the present invention was vacuum deposited to form a hole transport layer with a thickness of 60 nm. Then, on the hole transport layer, an emitting layer with a thickness of 30 nm was deposited using 9,10-di(naphthalen-2-yl)anthracene as a host and doped with BD-052X(Idemitsukosan) as a dopant in a weight ratio of 96:4. (1,1'-bisphenyl)-4-olato)bis(2-methyl-8-quinolinolato)aluminum (hereinafter will be abbreviated as BAlq) was vacuum deposited to form a hole blocking layer with a thickness of 10 nm, and an electron transport layer was formed by vacuum-depositing tris(8-quinolinol)aluminum (hereinafter will be abbreviated as Alq3) to a thickness of 40 nm. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manu-

TABLE 3

| compound | FD-MS | compound | FD-MS |
|---|---|---|---|
| 1-1 | m/z = 484.19($C_{36}H_{24}N_2$ = 484.59) | 1-2 | m/z = 534.21($C_{40}H_{26}N_2$ = 534.65) |
| 1-3 | m/z = 534.21($C_{40}H_{26}N_2$ = 534.65) | 1-4 | m/z = 636.26($C_{48}H_{32}N_2$ = 636.78) |
| 1-5 | m/z = 637.25($C_{47}H_{31}N_3$ = 637.77) | 1-6 | m/z = 676.29($C_{51}H_{36}N_2$ = 676.84) |
| 1-7 | m/z = 800.32($C_{61}H_{40}N_2$ = 800.98) | 1-8 | m/z = 798.30($C_{61}H_{38}N_2$ = 798.97) |
| 1-9 | m/z = 666.21($C_{48}H_{30}N_2S$ = 666.83) | 1-10 | m/z = 650.24($C_{48}H_{30}N_2O$ = 650.76) |
| 1-11 | m/z = 725.28($C_{54}H_{35}N_3$ = 725.88) | 1-12 | m/z = 584.23($C_{44}H_{28}N_2$ = 584.71) |
| 1-13 | m/z = 636.26($C_{48}H_{32}N_2$ = 636.78) | 1-14 | m/z = 636.26($C_{48}H_{32}N_2$ = 636.78) |
| 1-15 | m/z = 676.29($C_{51}H_{36}N_2$ = 676.84) | 1-16 | m/z = 676.29($C_{51}H_{36}N_2$ = 676.84) |
| 1-17 | m/z = 558.21($C_{42}H_{26}N_2$ = 558.67) | 1-18 | m/z = 723.27($C_{54}H_{33}N_3$ = 723.86) |
| 1-19 | m/z = 818.28($C_{60}H_{38}N_2S$ = 819.02) | 1-20 | m/z = 713.28($C_{53}H_{35}N_3$ = 713.87) |
| 1-21 | m/z = 560.23($C_{42}H_{28}N_2$ = 560.69) | 1-22 | m/z = 610.24($C_{46}H_{30}N_2$ = 610.74) |
| 1-23 | m/z = 610.24($C_{46}H_{30}N_2$ = 610.74) | 1-24 | m/z = 712.29($C_{54}H_{36}N_2$ = 712.88) |
| 1-25 | m/z = 713.28($C_{53}H_{35}N_3$ = 713.87) | 1-26 | m/z = 725.32($C_{57}H_{40}N_2$ = 752.94) |
| 1-27 | m/z = 876.35($C_{67}H_{44}N_2$ = 877.08) | 1-28 | m/z = 874.33($C_{67}H_{42}N_2$ = 875.06) |
| 1-29 | m/z = 742.24($C_{54}H_{34}N_2S$ = 742.93) | 1-30 | m/z = 726.27($C_{54}H_{34}N_2O$ = 726.86) |
| 1-31 | m/z = 801.31($C_{60}H_{39}N_3$ = 801.97) | 1-32 | m/z = 610.24($C_{46}H_{30}N_2$ = 610.74) |
| 1-33 | m/z = 788.32($C_{60}H_{40}N_2$ = 788.97) | 1-34 | m/z = 953.38($C_{72}H_{47}N_3$ = 954.16) |
| 1-35 | m/z = 740.23($C_{54}H_{32}N_2S$ = 740.91) | 1-36 | m/z = 635.24($C_{47}H_{29}N_3$ = 635.75) |
| 2-1 | m/z = 484.19($C_{36}H_{24}N_2$ = 484.59) | 2-2 | m/z = 534.21($C_{40}H_{26}N_2$ = 534.65) |
| 2-3 | m/z = 534.21($C_{40}H_{26}N_2$ = 534.65) | 2-4 | m/z = 636.26($C_{48}H_{32}N_2$ = 636.78) |
| 2-5 | m/z = 637.25($C_{47}H_{31}N_3$ = 637.77) | 2-6 | m/z = 676.29($C_{51}H_{36}N_2$ = 676.84) |
| 2-7 | m/z = 800.32($C_{61}H_{40}N_2$ = 800.98) | 2-8 | m/z = 798.30($C_{61}H_{38}N_2$ = 798.97) |
| 2-9 | m/z = 666.21($C_{48}H_{30}N_2S$ = 666.83) | 2-10 | m/z = 650.24($C_{48}H_{30}N_2O$ = 650.76) |
| 2-11 | m/z = 725.28($C_{54}H_{35}N_3$ = 725.88) | 2-12 | m/z = 584.23($C_{44}H_{28}N_2$ = 584.71) |
| 2-13 | m/z = 818.28($C_{60}H_{38}N_2S$ = 819.02) | 2-14 | m/z = 713.28($C_{53}H_{35}N_3$ = 713.87) |
| 2-15 | m/z = 712.29($C_{54}H_{36}N_2$ = 712.88) | 2-16 | m/z = 877.35($C_{66}H_{43}N_3$ = 878.07) |
| 2-17 | m/z = 560.23($C_{42}H_{28}N_2$ = 560.69) | 2-18 | m/z = 610.24($C_{46}H_{30}N_2$ = 610.74) |
| 2-19 | m/z = 610.24($C_{46}H_{30}N_2$ = 610.74) | 2-20 | m/z = 712.29($C_{54}H_{36}N_2$ = 712.88) |
| 2-21 | m/z = 713.28($C_{53}H_{35}N_3$ = 713.87) | 2-22 | m/z = 752.32($C_{57}H_{40}N_2$ = 752.94) |
| 2-23 | m/z = 876.35($C_{67}H_{44}N_2$ = 877.08) | 2-24 | m/z = 874.33($C_{67}H_{42}N_2$ = 875.06) |
| 2-25 | m/z = 742.24($C_{54}H_{34}N_2S$ = 742.93) | 2-26 | m/z = 762.27($C_{54}H_{34}N_2O$ = 726.86) |
| 2-27 | m/z = 801.31($C_{60}H_{39}N_3$ = 801.97) | 2-28 | m/z = 610.24($C_{46}H_{30}N_2$ = 610.74) |
| 2-29 | m/z = 788.32($C_{60}H_{40}N_2$ = 788.97) | 2-30 | m/z = 953.38($C_{72}H_{47}N_3$ = 954.16) |
| 2-31 | m/z = 740.23($C_{54}H_{32}N_2S$ = 740.91) | 2-32 | m/z = 635.24($C_{47}H_{29}N_3$ = 635.75) |
| 2-33 | m/z = 560.23($C_{42}H_{28}N_2$ = 560.69) | 2-34 | m/z = 610.24($C_{46}H_{30}N_2$ = 610.74) |
| 2-35 | m/z = 610.24($C_{46}H_{30}N_2$ = 610.74) | 2-36 | m/z = 712.29($C_{54}H_{36}N_2$ = 712.88) | factured by McScience Inc. with a reference luminance of 500 cd/m². In the following table, the manufacture of a device and the results of evaluation are shown.

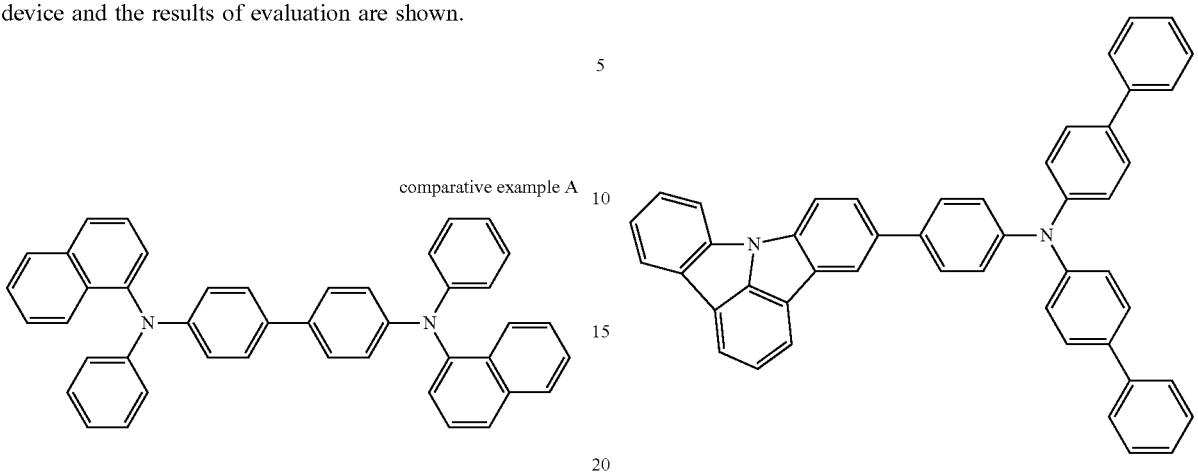

comparative example A comparative example B

TABLE 4

| | compound | Voltage | Current Density | Brightness (cd/m2) | Efficiency | Lifetime T(95) | CIE (x, y) |
|---|---|---|---|---|---|---|---|
| Comparative example(1) | compound (A) | 5.7 | 14.3 | 500.0 | 3.5 | 52.4 | (0.15, 0.13) |
| Comparative example(2) | compound (B) | 5.3 | 10.9 | 500.0 | 4.6 | 87.8 | (0.14, 0.14) |
| example(1) | compound(1-1) | 4.2 | 8.4 | 500.0 | 5.9 | 113.4 | (0.15, 0.13) |
| example(2) | compound(1-2) | 4.1 | 8.8 | 500.0 | 5.7 | 113.0 | (0.15, 0.14) |
| example(3) | compound(1-3) | 4.1 | 8.5 | 500.0 | 5.9 | 102.6 | (0.15, 0.13) |
| example(4) | compound(1-4) | 4.1 | 8.4 | 500.0 | 5.9 | 105.7 | (0.14, 0.14) |
| example(5) | compound(1-5) | 4.0 | 8.7 | 500.0 | 5.8 | 106.4 | (0.14, 0.14) |
| example(6) | compound(1-6) | 4.0 | 9.0 | 500.0 | 5.6 | 103.9 | (0.14, 0.14) |
| example(7) | compound(1-7) | 4.3 | 9.0 | 500.0 | 5.6 | 118.1 | (0.15, 0.13) |
| example(8) | compound(1-8) | 4.3 | 8.4 | 500.0 | 5.9 | 113.8 | (0.15, 0.13) |
| example(9) | compound(1-9) | 4.5 | 8.6 | 500.0 | 5.8 | 103.8 | (0.15, 0.14) |
| example(10) | compound(1-10) | 4.2 | 8.5 | 500.0 | 5.9 | 104.7 | (0.15, 0.13) |
| example(11) | compound(1-11) | 4.0 | 8.4 | 500.0 | 5.9 | 109.3 | (0.15, 0.13) |
| example(12) | compound(1-12) | 4.1 | 8.6 | 500.0 | 5.8 | 102.6 | (0.14, 0.14) |
| example(13) | compound(1-13) | 4.1 | 8.4 | 500.0 | 5.9 | 104.8 | (0.15, 0.14) |
| example(14) | compound(1-14) | 4.3 | 8.9 | 500.0 | 5.6 | 100.9 | (0.15, 0.14) |
| example(15) | compound(1-15) | 4.2 | 8.7 | 500.0 | 5.8 | 110.9 | (0.14, 0.14) |
| example(16) | compound(1-16) | 4.1 | 8.9 | 500.0 | 5.6 | 111.3 | (0.15, 0.13) |
| example(17) | compound(1-17) | 4.1 | 9.0 | 500.0 | 5.6 | 114.9 | (0.15, 0.16) |
| example(18) | compound(1-18) | 4.3 | 8.7 | 500.0 | 5.7 | 118.2 | (0.15, 0.14) |
| example(19) | compound(1-19) | 4.2 | 9.0 | 500.0 | 5.6 | 117.8 | (0.15, 0.13) |
| example(20) | compound(1-20) | 4.3 | 9.0 | 500.0 | 5.6 | 102.7 | (0.14, 0.14) |
| example(21) | compound(1-21) | 4.4 | 8.6 | 500.0 | 5.8 | 110.6 | (0.15, 0.14) |
| example(22) | compound(1-22) | 4.3 | 8.4 | 500.0 | 6.0 | 106.5 | (0.15, 0.13) |
| example(23) | compound(1-23) | 4.4 | 8.6 | 500.0 | 5.8 | 112.8 | (0.15, 0.14) |
| example(24) | compound(1-24) | 4.5 | 8.9 | 500.0 | 5.6 | 111.9 | (0.15, 0.13) |
| example(25) | compound(1-25) | 4.5 | 8.6 | 500.0 | 5.8 | 110.4 | (0.14, 0.14) |
| example(26) | compound(1-26) | 4.1 | 8.7 | 500.0 | 5.8 | 111.3 | (0.14, 0.14) |
| example(27) | compound(1-27) | 4.1 | 8.9 | 500.0 | 5.6 | 100.7 | (0.14, 0.14) |
| example(28) | compound(1-28) | 4.4 | 8.4 | 500.0 | 5.9 | 118.9 | (0.15, 0.13) |
| example(29) | compound(1-29) | 4.1 | 8.7 | 500.0 | 5.8 | 107.0 | (0.15, 0.14) |
| example(30) | compound(1-30) | 4.4 | 8.4 | 500.0 | 6.0 | 117.9 | (0.15, 0.14) |
| example(31) | compound(1-31) | 4.3 | 8.5 | 500.0 | 5.9 | 108.9 | (0.15, 0.13) |
| example(32) | compound(1-32) | 4.1 | 9.1 | 500.0 | 5.5 | 118.2 | (0.15, 0.13) |
| example(33) | compound(1-33) | 4.3 | 8.9 | 500.0 | 5.6 | 104.8 | (0.14, 0.14) |
| example(34) | compound(1-34) | 4.4 | 8.4 | 500.0 | 5.9 | 111.1 | (0.15, 0.14) |
| example(35) | compound(1-35) | 4.3 | 8.9 | 500.0 | 5.6 | 115.3 | (0.15, 0.14) |
| example(36) | compound(1-36) | 4.2 | 8.5 | 500.0 | 5.9 | 102.5 | (0.14, 0.14) |
| example(61) | compound(2-1) | 5.0 | 9.2 | 500.0 | 5.4 | 100.5 | (0.14, 0.14) |
| example(62) | compound(2-2) | 4.9 | 9.3 | 500.0 | 5.4 | 103.3 | (0.15, 0.13) |
| example(63) | compound(2-3) | 4.9 | 9.6 | 500.0 | 5.2 | 106.8 | (0.15, 0.13) |
| example(64) | compound(2-4) | 4.7 | 9.4 | 500.0 | 5.3 | 105.1 | (0.15, 0.14) |
| example(65) | compound(2-5) | 4.9 | 9.5 | 500.0 | 5.3 | 109.5 | (0.15, 0.14) |
| example(66) | compound(2-6) | 4.9 | 9.6 | 500.0 | 5.2 | 116.6 | (0.15, 0.14) |
| example(67) | compound(2-7) | 4.8 | 9.6 | 500.0 | 5.2 | 105.8 | (0.15, 0.13) |
| example(68) | compound(2-8) | 5.0 | 9.6 | 500.0 | 5.2 | 112.2 | (0.15, 0.13) |
| example(69) | compound(2-9) | 4.6 | 9.9 | 500.0 | 5.0 | 118.0 | (0.15, 0.14) |
| example(70) | compound(2-10) | 4.6 | 9.6 | 500.0 | 5.2 | 109.8 | (0.15, 0.15) |

TABLE 4-continued

| | compound | Voltage | Current Density | Brightness (cd/m2) | Efficiency | Lifetime T(95) | CIE (x, y) |
|---|---|---|---|---|---|---|---|
| example(71) | compound(2-11) | 4.9 | 9.6 | 500.0 | 5.2 | 114.5 | (0.15, 0.15) |
| example(72) | compound(2-12) | 4.7 | 9.9 | 500.0 | 5.1 | 101.5 | (0.15, 0.14) |
| example(73) | compound(2-13) | 4.7 | 9.4 | 500.0 | 5.3 | 113.5 | (0.15, 0.14) |
| example(74) | compound(2-14) | 4.9 | 9.1 | 500.0 | 5.5 | 110.7 | (0.15, 0.16) |
| example(75) | compound(2-15) | 4.8 | 9.7 | 500.0 | 5.1 | 105.8 | (0.14, 0.14) |
| example(76) | compound(2-16) | 4.6 | 9.2 | 500.0 | 5.4 | 101.5 | (0.15, 0.13) |
| example(77) | compound(2-17) | 4.7 | 9.6 | 500.0 | 5.2 | 100.7 | (0.15, 0.14) |
| example(78) | compound(2-18) | 5.0 | 9.9 | 500.0 | 5.1 | 102.8 | (0.15, 0.13) |
| example(79) | compound(2-19) | 4.9 | 9.3 | 500.0 | 5.4 | 100.8 | (0.14, 0.14) |
| example(80) | compound(2-20) | 5.0 | 9.4 | 500.0 | 5.3 | 107.6 | (0.14, 0.14) |
| example(81) | compound(2-21) | 4.7 | 9.9 | 500.0 | 5.1 | 109.7 | (0.15, 0.13) |
| example(82) | compound(2-22) | 5.0 | 9.8 | 500.0 | 5.1 | 111.7 | (0.15, 0.14) |
| example(83) | compound(2-23) | 4.8 | 9.4 | 500.0 | 5.3 | 102.0 | (0.15, 0.14) |
| example(84) | compound(2-24) | 4.5 | 9.9 | 500.0 | 5.0 | 106.5 | (0.15, 0.13) |
| example(85) | compound(2-25) | 4.8 | 9.8 | 500.0 | 5.1 | 109.7 | (0.14, 0.14) |
| example(86) | compound(2-26) | 4.7 | 9.1 | 500.0 | 5.5 | 102.1 | (0.15, 0.14) |
| example(87) | compound(2-27) | 4.6 | 9.2 | 500.0 | 5.4 | 111.8 | (0.15, 0.14) |
| example(88) | compound(2-28) | 4.9 | 9.4 | 500.0 | 5.3 | 105.2 | (0.14, 0.14) |
| example(89) | compound(2-29) | 4.6 | 9.4 | 500.0 | 5.3 | 113.5 | (0.15, 0.13) |
| example(90) | compound(2-30) | 4.8 | 10.0 | 500.0 | 5.0 | 105.6 | (0.15, 0.16) |
| example(91) | compound(2-31) | 4.9 | 9.6 | 500.0 | 5.2 | 100.7 | (0.15, 0.14) |
| example(92) | compound(2-32) | 4.8 | 9.7 | 500.0 | 5.1 | 109.2 | (0.14, 0.14) |
| example(93) | compound(2-33) | 4.5 | 9.7 | 500.0 | 5.2 | 106.6 | (0.14, 0.14) |
| example(94) | compound(2-34) | 4.6 | 9.9 | 500.0 | 5.0 | 106.3 | (0.15, 0.14) |
| example(95) | compound(2-35) | 4.7 | 9.6 | 500.0 | 5.2 | 114.0 | (0.15, 0.13) |
| example(96) | compound(2-36) | 5.0 | 9.2 | 500.0 | 5.4 | 116.4 | (0.15, 0.15) |

As it is apparent from the results of Table 4, when the compound of the present invention is used as hole transport layer, the driving voltage and life span can be remarkably improved.

Otherwise, Comparative Example using Comparative Compound 2 in which indolocarbazole is a core as a hole transport layer showed improved device results in terms of driving voltage, efficiency, and lifetime than Comparative Example 1 using NPB as a hole transport layer.

Inventive Compounds 2-1 to 36 are substituted with the 5-position of indolecarbazole in the same manner as the comparative compound but have a non-linear substituent, and have a higher T1 value because the bonding angle is smaller than that of Comparative Compound 2 having a linear substituent, and therefore, it is judged that the electronic blocking ability is improved, and Inventive Compounds 1-1-35 are linked to a non-linear substituent at position 6 of indolocarbazole and are shorter than those in the case where conjugation length is connected to position 5, as a result, the band gap is widened and the HOMO value becomes deep. As a result, the exciton is more easily generated in the emitting layer due to the deep HOMO value and the improved electron blocking ability, and therefore, it is considered that the device using the compound of the present invention has improved efficiency and life span and lowered the driving voltage.

Example 2) Manufacture and Test of Red OLED (Emitting Auxiliary Layer)

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenylbenzene-1,4-diamine (hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. Then, the inventive compounds (1-1 to 2-36) were vacuum deposited to form an emitting auxiliary layer with a thickness of 20 nm. On the emitting auxiliary layer, an emitting layer with a thickness of 30 nm was deposited using CBP as a host and doped with (piq)$_2$Ir(acac) [bis-(1-phenylisoquinolyl)iridium(III)acetylacetonate] as a dopant in a weight ratio of 95:5. (1,1'-bisphenyl)-4-olato) bis(2-methyl-8-quinolinolato)aluminum (hereinafter will be abbreviated as BAlq) was vacuum deposited to form a hole blocking layer with a thickness of 10 nm, and an electron transport layer was formed using tris(8-quinolinol)aluminum (hereinafter will be abbreviated as Alq3) to a thickness of 40 nm. After that, an alkali metal halide, LiF was deposited as an electron injection layer to a thickness of 0.2 nm, and Al was deposited as a cathode to a thickness of 150 nm to manufacture an OLED.

To the OLEDs which were manufactured in examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m². In the following table, the results on the manufacture of a device and evaluation are shown.

Comparative Example 3

Except for not using the emitting auxiliary layer, an OLED was manufactured in the same manner as described in the example 2 above.

Comparative Example 4 and Comparative Example 5)

Except that the comparative compound (1) and (2) was used as the emitting auxiliary layer, an OLED was manufactured in the same manner as described in the example 2 above.

TABLE 5

| | compound | Voltage | Current Density | Brightness (cd/m2) | Efficiency | Lifetime T(95) | CIE (x, y) |
|---|---|---|---|---|---|---|---|
| Comparative example (3) | — | 6.5 | 32.9 | 2500.0 | 7.6 | 69.5 | (0.66, 0.32) |
| Comparative example (4) | Comparative compound (1) | 6.7 | 26.9 | 2500.0 | 9.3 | 86.0 | (0.66, 0.32) |
| Comparative example (5) | Comparative compound (2) | 6.6 | 25.3 | 2500.0 | 9.9 | 98.5 | (0.67, 0.32) |
| example(97) | compound(1-2) | 6.2 | 15.4 | 2500.0 | 16.3 | 111.5 | (0.65, 0.32) |
| example(98) | compound(1-9) | 6.2 | 14.3 | 2500.0 | 17.5 | 118.6 | (0.66, 0.32) |
| example(99) | compound(1-14) | 6.3 | 15.1 | 2500.0 | 16.5 | 114.9 | (0.66, 0.33) |
| example(100) | compound(1-24) | 6.3 | 14.1 | 2500.0 | 17.7 | 110.9 | (0.66, 0.32) |
| example(101) | compound(1-28) | 6.2 | 15.3 | 2500.0 | 16.4 | 117.5 | (0.65, 0.32) |
| example(102) | compound(1-29) | 6.2 | 15.8 | 2500.0 | 15.8 | 111.7 | (0.66, 0.32) |
| example(103) | compound(1-32) | 6.3 | 14.0 | 2500.0 | 17.8 | 116.2 | (0.66, 0.32) |
| example(104) | compound(1-41) | 6.3 | 13.9 | 2500.0 | 18.0 | 113.0 | (0.67, 0.32) |
| example(105) | compound(2-6) | 6.3 | 17.5 | 2500.0 | 14.3 | 113.9 | (0.66, 0.32) |
| example(106) | compound(2-9) | 6.4 | 17.8 | 2500.0 | 14.0 | 113.6 | (0.66, 0.32) |
| example(107) | compound(2-20) | 6.4 | 18.5 | 2500.0 | 13.5 | 112.7 | (0.66, 0.33) |
| example(108) | compound(2-33) | 6.4 | 18.6 | 2500.0 | 13.4 | 112.2 | (0.66, 0.32) |

As it is apparent from the results of Table 5, when a red organic electroluminescent device is manufactured using materials for organic electric elements of the present invention as an emitting auxiliary layer material, the driving voltage of the organic electroluminescence device can be lowered and the luminous efficiency and life span can be remarkably improved as compared with the comparative examples not using the emitting auxiliary layer or using the comparative compounds 1,2.

As shown in Table 4, when the compound of the present invention is used alone as an emitting auxiliary layer, it has a high T1 energy level and a deep HOMO energy level, as a result, it is believed that the hole and electron have a charge balance, and light emission is performed inside the emitting layer rather than at the interface of the hole transporting layer, driving voltage is lowered, and efficiency and lifetime are maximized.

As described above, it can be confirmed that similar tendency is exhibited by acting as a main factor in improving the device performance in the hole transport layer as well as the emitting auxiliary layer depending on the bonding position and the kind of the substituent (linear or non-linear).

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula (3):

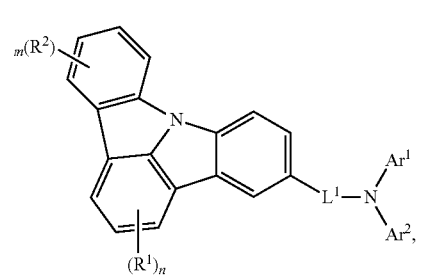

Formula_(3)

wherein:
1) $Ar^1$ and $Ar^2$ are each independently a $C_6$-$C_{25}$ aromatic hydrocarbon group or a fluorenyl group,
2) $L^1$ is selected from the group consisting of the following Formulas (A-1) and (A-3) to (A-5):

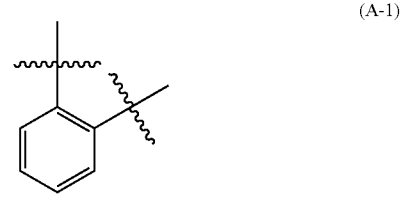

(A-1)

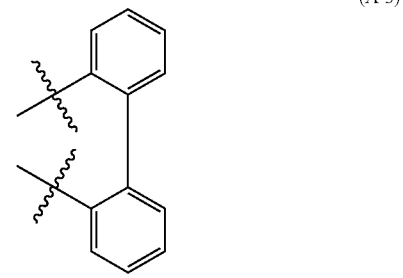

(A-3)

-continued

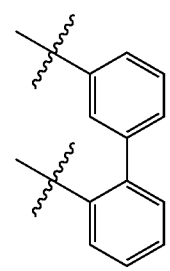
(A-4)

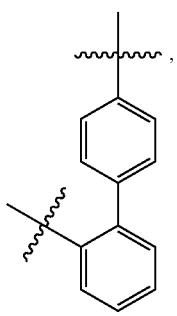
(A-5)

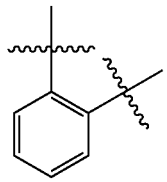
(A-1)

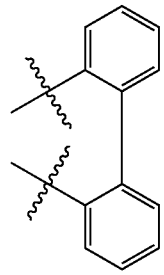
(A-3)

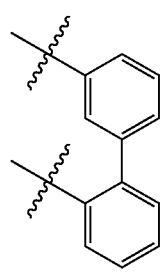
(A-4)

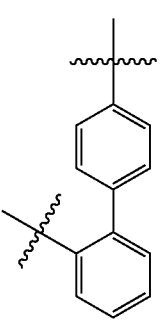
(A-5)

3) m is an integer of 0 to 4, n is an integer of 0 to 3, and R$^1$ and R$^2$ are the same or different from each other and are each independently selected from the group consisting of a deuterium; a halogen; a C$_6$-C$_{25}$ aryl group; a fluorenyl group; a C$_2$-C$_{25}$ heterocyclic group including at least one hetero atom of O, N, S, Si and P, and in the case where m and n are each 2 or more and thereby R$^1$ and R$^2$ are each in plural, same or different, a plurality of R$^1$ or a plurality of R$^2$ may be bonded to each other to form a ring, wherein the aryl or aromatic hydrocarbon group, the hetero aryl group, the fluorenyl group, and the arylene group, may be substituted by one or more of the substituents selected from the group consisting of deuterium; halogen; a C$_1$-C$_{20}$ alkyl group; a C$_6$-C$_{20}$ aryl group.

2. A compound represented by Formula (2):

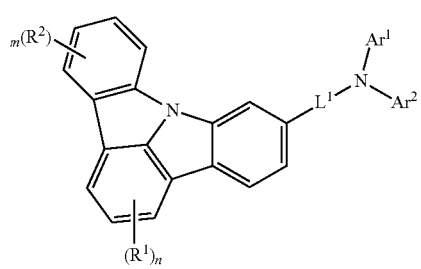

Formula_(2)

wherein:

1) Ar$^1$ and Ar$^2$ are each independently selected from the group consisting of a C$_6$-C$_{25}$ aryl group; a fluorenyl group; a C$_2$-C$_{25}$ heterocyclic group including at least one hetero atom of O, N, S, Si and P;

2) L$^1$ is selected from the group consisting of Formulas (A-1) and (A-3) to (A-5)

3) m is an integer of 0 to 4, n is an integer of 0 to 3, and m+n is at least 1,

4) R$^1$ and R$^2$ are the same or different from each other and are each independently a C$_6$-C$_{25}$ aryl group or a C$_2$-C$_{25}$ heterocyclic group including at least one hetero atom of O, N, S, Si and P; and in case m and n are 2 or more and therefore R$^1$ and R$^2$ are each in plural, same or different, a plurality of R$^1$ or a plurality of R$^2$ may be bonded to each other to form a benzene ring, wherein the aryl group, the hetero aryl group, the fluorenyl group, and the arylene group may be substituted by one or more of the substituents selected from the group consisting of deuterium; halogen; a C$_1$-C$_{20}$ alkyl group; a C$_6$-C$_{20}$ aryl group.

3. A compound selected from the group consisting of the following compounds:

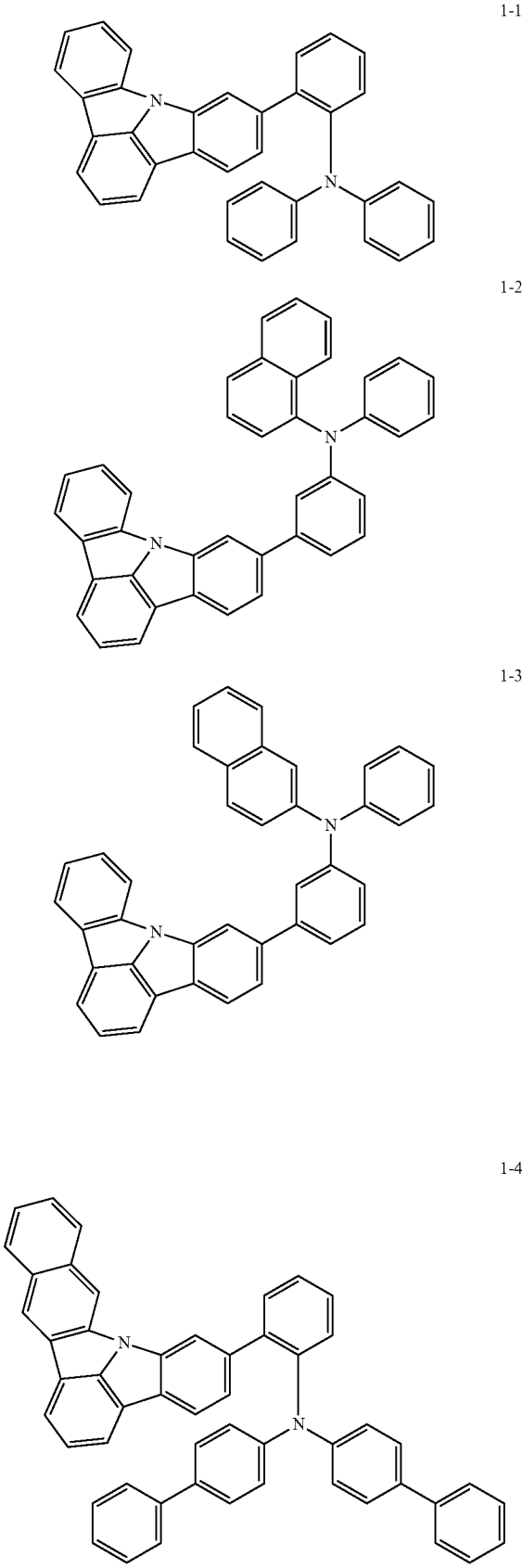

1-8
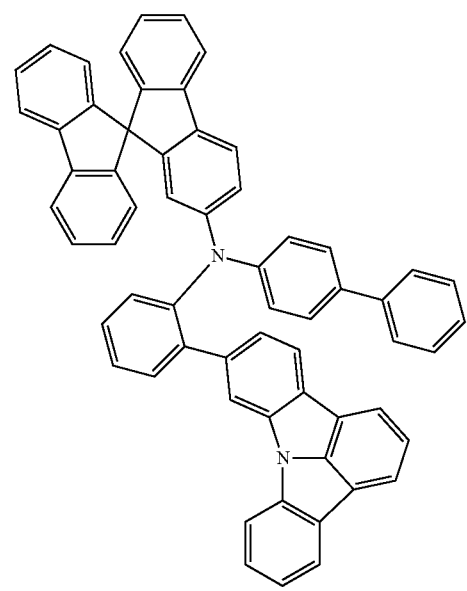
1-9
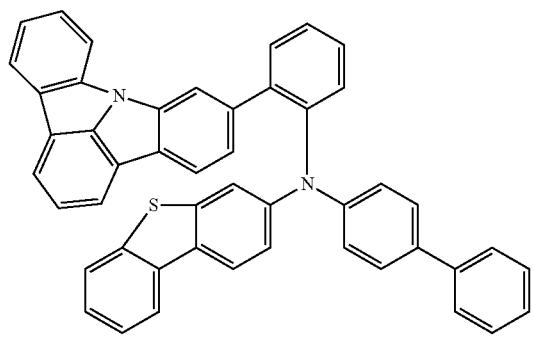
1-10
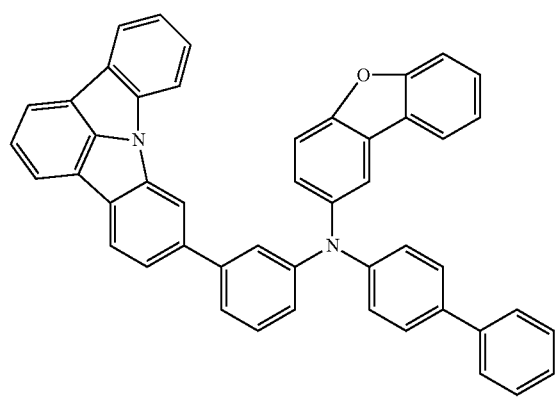
1-11
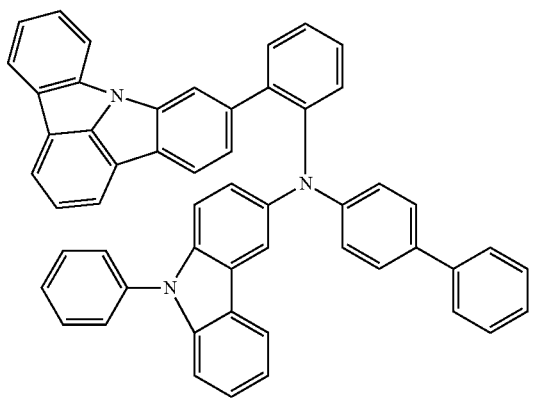
1-12
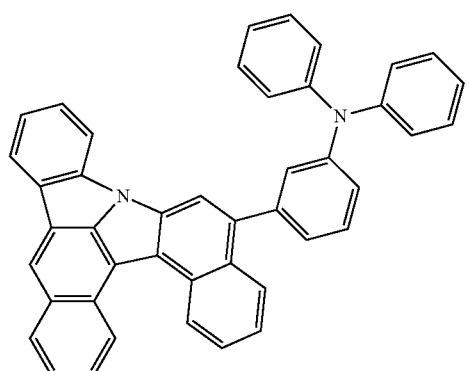
1-13
1-14
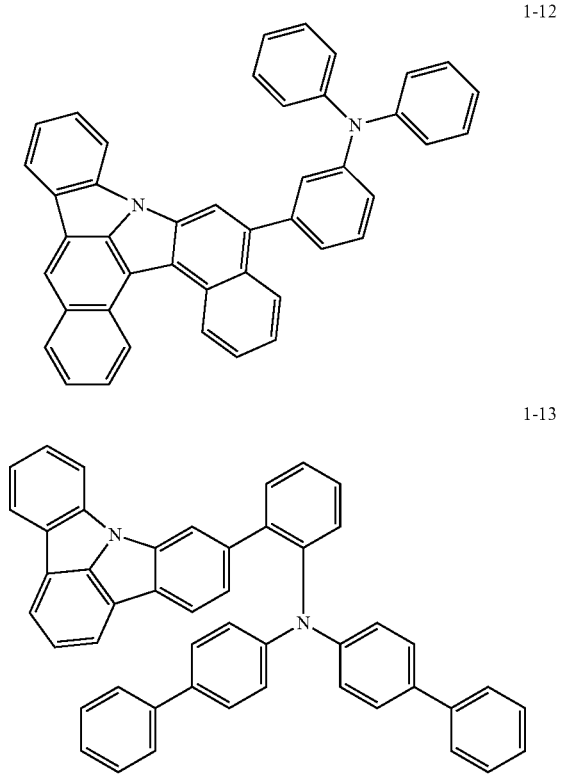

1-15
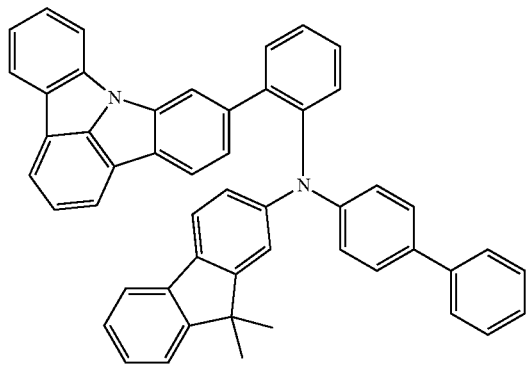
1-16
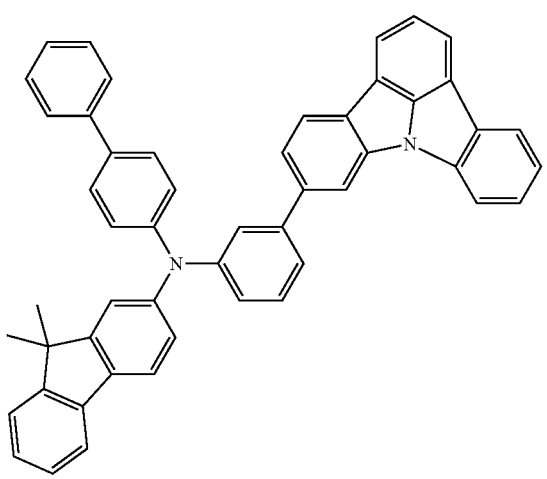
1-17
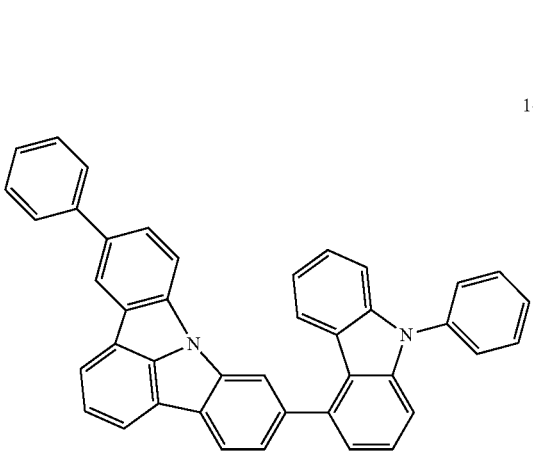
1-18
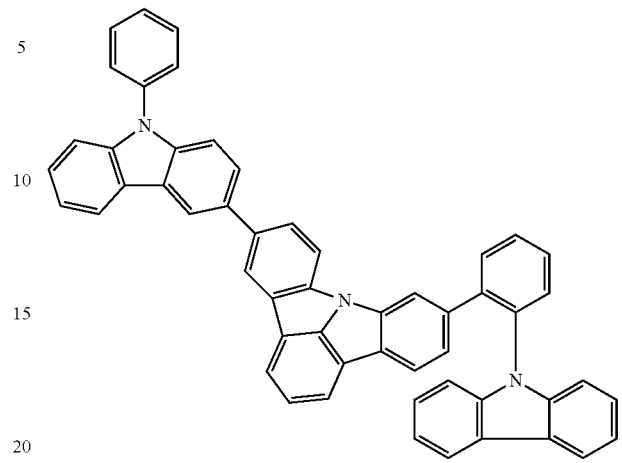
1-19
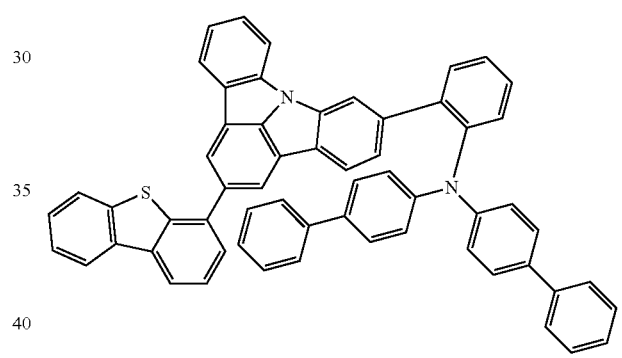
1-20
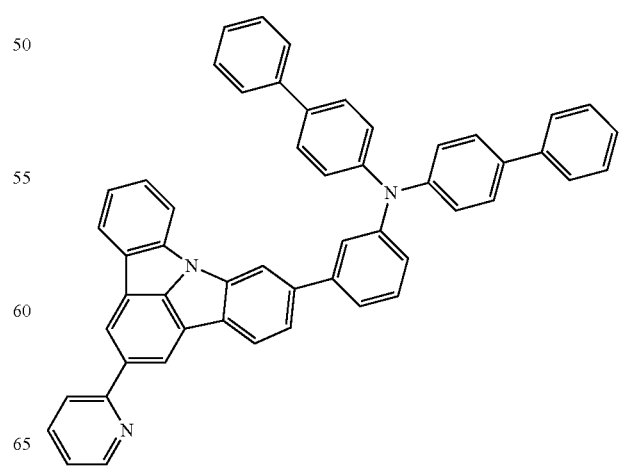

1-32
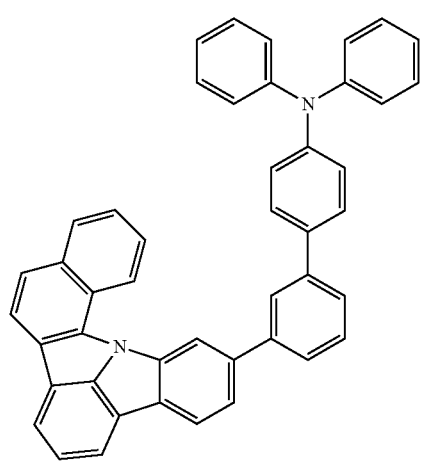
1-35
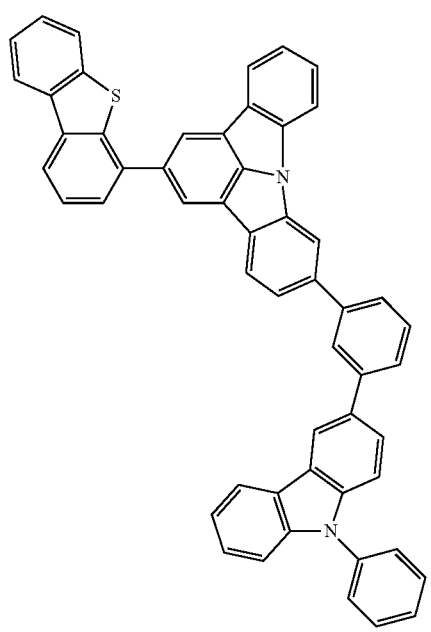
1-33
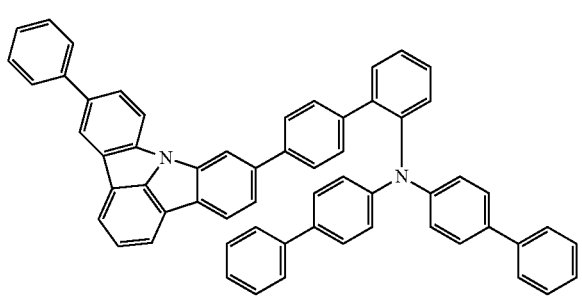
1-36
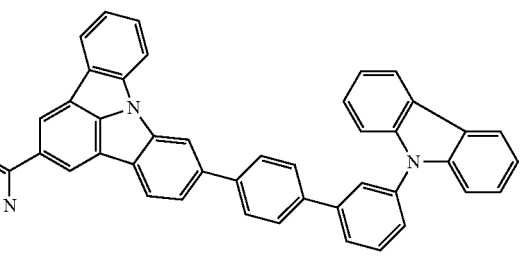
2-1
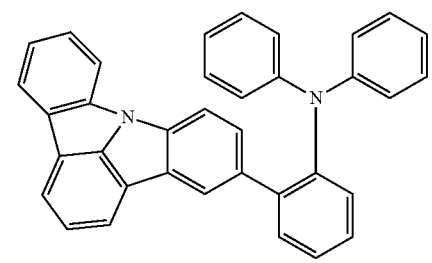
1-34
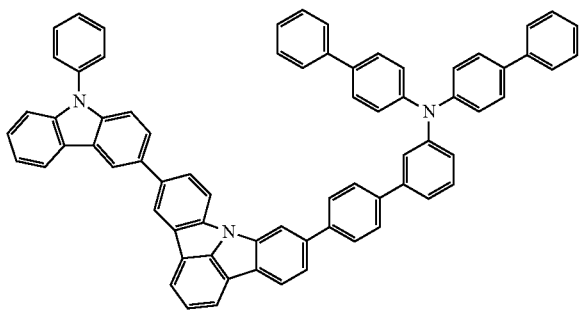
2-2

2-3
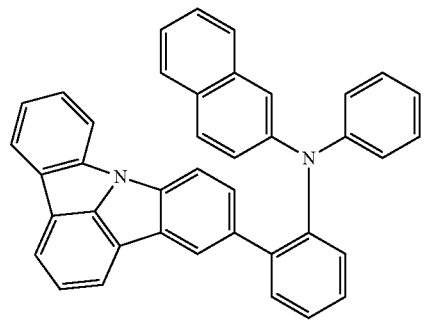
2-4
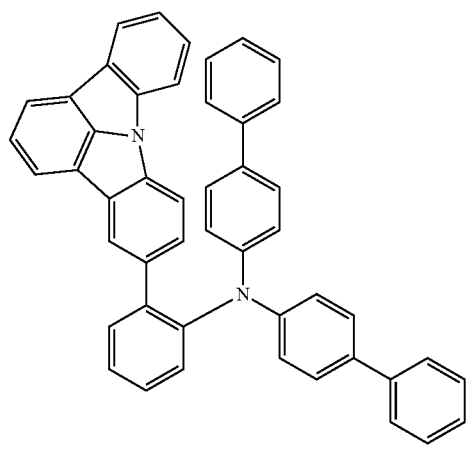
2-5
2-12
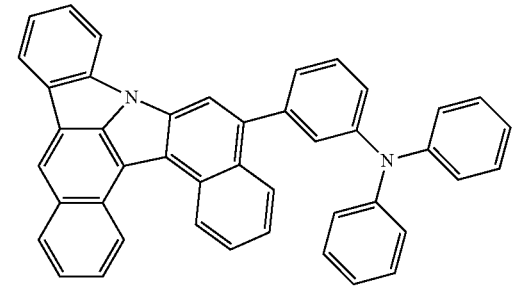
2-13
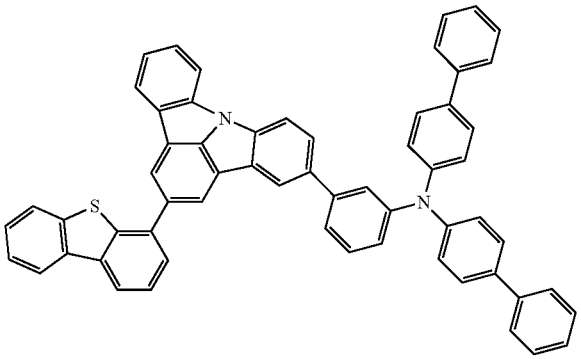
2-14
2-15
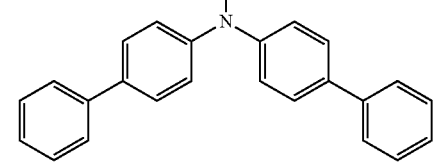

2-16
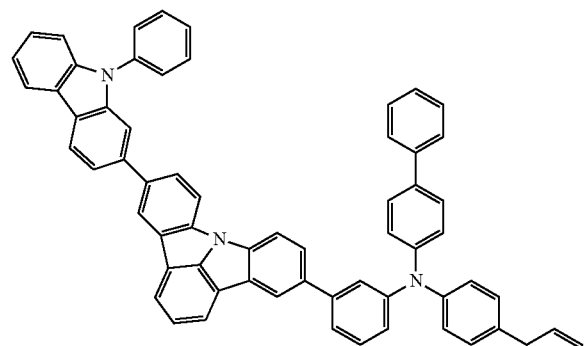
2-17
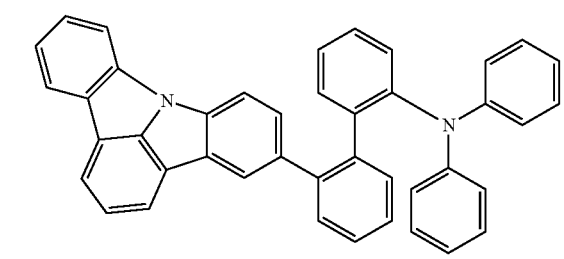
2-18
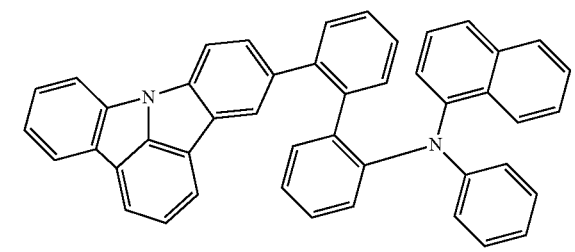
2-19
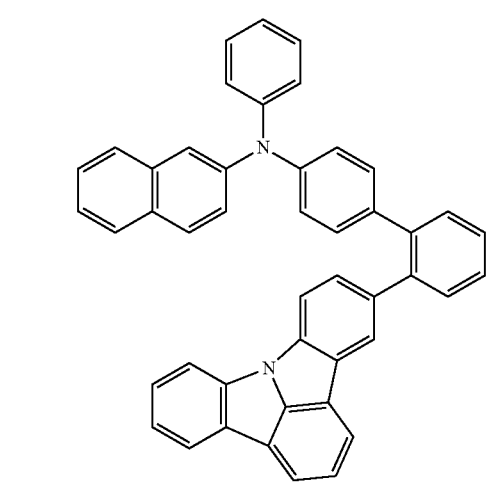
2-20
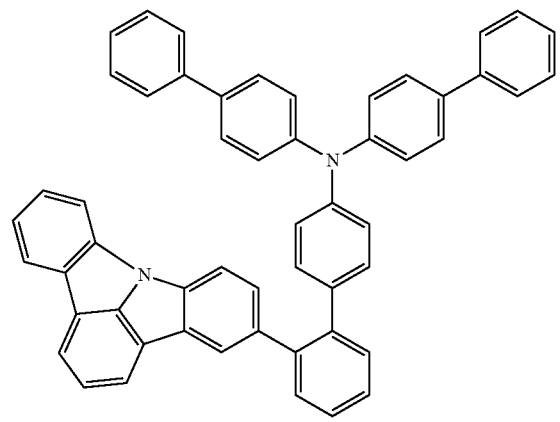
2-21
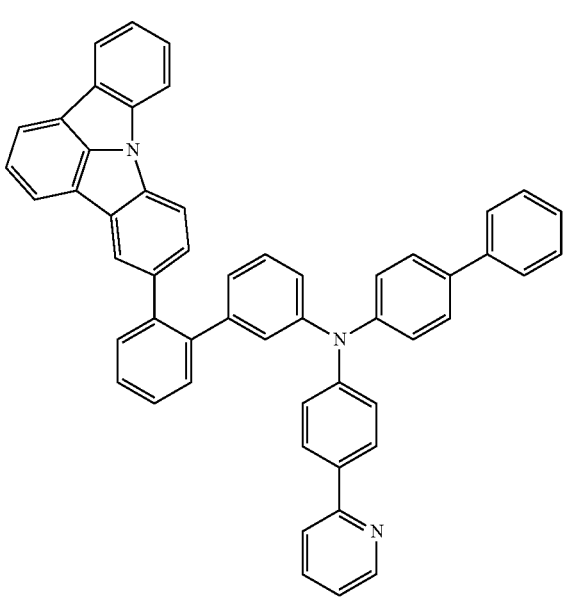
2-22
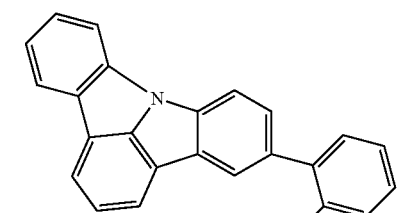
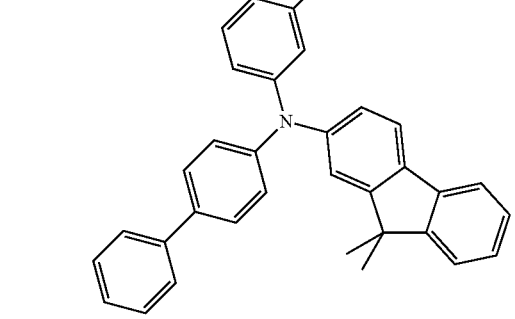

2-23
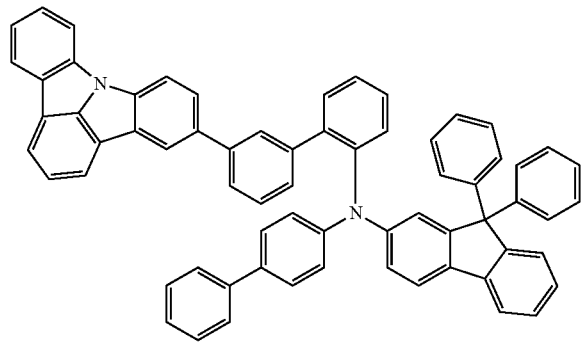
2-30
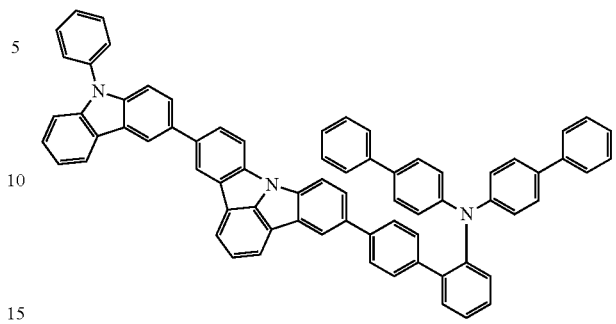
2-24
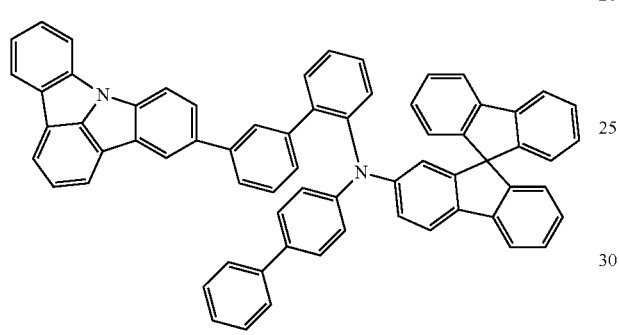
2-31
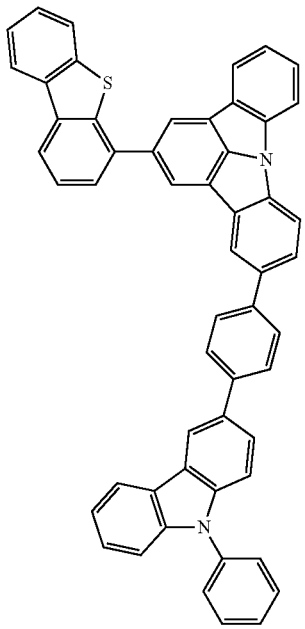
2-28
2-29
2-32
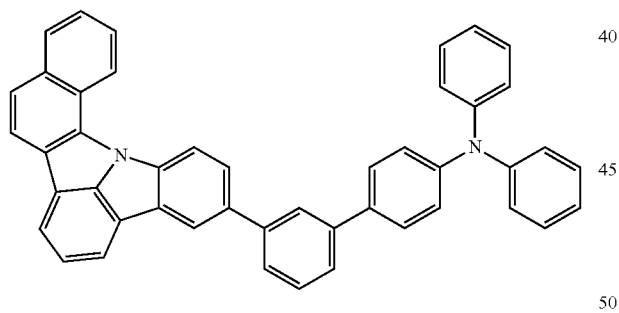
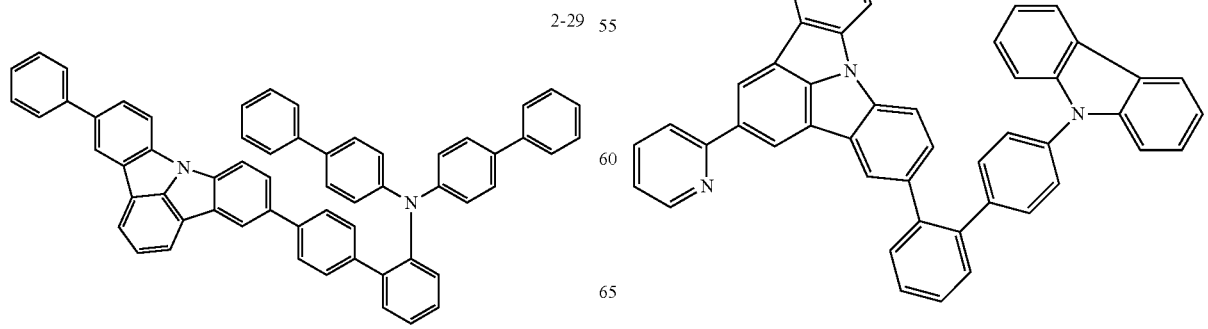

-continued 2-35
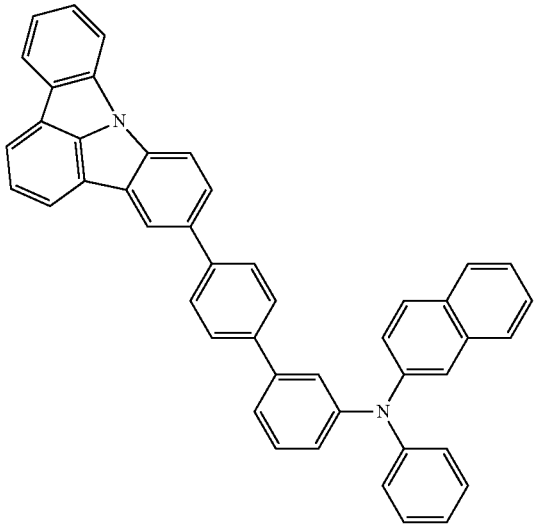

2-36
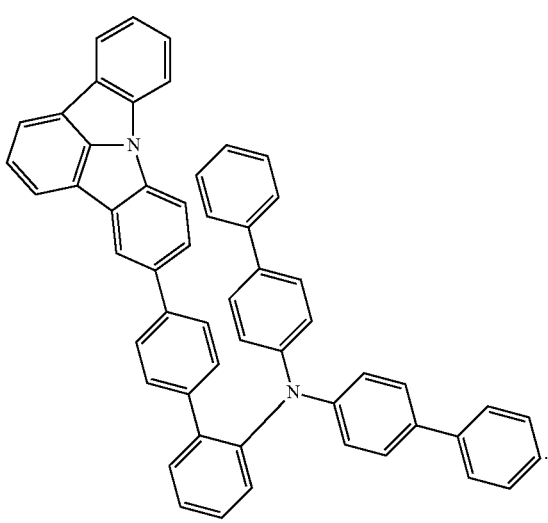

4. A composition for a hole transport layer or an emitting auxiliary layer of an organic electric device, comprising the compound according to claim 1.

5. An organic electric element comprising: a first electrode, a second electrode, and an organic material layer formed between the first electrode and the second electrode, wherein the organic material layer comprises the compound according to claim 1.

6. The organic electric element of claim 5, further comprising a light efficiency enhancing layer formed on the side of the first electrode and/or the side of the second electrode, the side being an opposite side not facing the organic material layer.

7. The organic electric element of claim 5, wherein the organic material layer is formed by a spin coating process, a nozzle printing process, an inkjet printing process, a slot coating process, a dip coating process, or a roll-to-roll process.

8. The organic electric element of claim 5, wherein the organic material layer is a hole transport layer or an emitting auxiliary layer.

9. An electronic device comprising: a display device including the organic electric element of claim 6; and a control unit for driving the display device.

10. The electronic device of claim 9, wherein the organic electric element is at least one of an OLED, an organic solar cell, an organic photo conductor, an organic transistor, and an element for monochromic or white illumination.

11. An organic electric element comprising:
a first electrode, a second electrode, and an organic material layer formed between the first electrode and the second electrode, wherein the organic material layer comprises the compound according to claim 2.

12. An electronic device comprising: a display device including the organic electric element of claim 11; and a control unit for driving the display device.

13. An organic electric element comprising:
a first electrode, a second electrode, and an organic material layer formed between the first electrode and the second electrode, wherein the organic material layer comprises the compound according to claim 3.

14. An electronic device comprising: a display device including the organic electric element of claim 13; and a control unit for driving the display device.

\* \* \* \* \*